(12) United States Patent
Krusemark et al.

(10) Patent No.: US 11,028,427 B2
(45) Date of Patent: Jun. 8, 2021

(54) SYSTEMS AND METHODS FOR PROTEOMIC ACTIVITY ANALYSIS USING DNA-ENCODED PROBES

(71) Applicant: Purdue Research Foundation, West Lafayette, IN (US)

(72) Inventors: Casey J. Krusemark, West Lafayette, IN (US); Kyle E. Denton, Shawnee, KS (US); Dongwook Kim, West Lafayette, IN (US); Rachael R. Jetson, Belmont, MA (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/753,317

(22) PCT Filed: Aug. 18, 2016

(86) PCT No.: PCT/US2016/047654
§ 371 (c)(1),
(2) Date: Feb. 18, 2018

(87) PCT Pub. No.: WO2017/031378
PCT Pub. Date: Feb. 23, 2017

(65) Prior Publication Data
US 2018/0237831 A1    Aug. 23, 2018

Related U.S. Application Data

(60) Provisional application No. 62/206,836, filed on Aug. 18, 2015.

(51) Int. Cl.
| | | |
|---|---|---|
| *C12Q 1/6823* | (2018.01) | |
| *C12N 15/10* | (2006.01) | |
| *C07H 21/04* | (2006.01) | |
| *C12Q 1/686* | (2018.01) | |
| *G01N 33/68* | (2006.01) | |

(52) U.S. Cl.
CPC ........... *C12Q 1/6823* (2013.01); *C07H 21/04* (2013.01); *C12N 15/1065* (2013.01); *C12N 15/1075* (2013.01); *C12Q 1/686* (2013.01); *G01N 33/68* (2013.01); *C12N 2310/3517* (2013.01); *C12N 2320/10* (2013.01)

(58) Field of Classification Search
CPC ...... C12Q 1/6823; C12Q 1/686; C07H 21/04; C12N 15/1065; C12N 15/1075; C12N 2310/3517; C12N 2320/10; G01N 33/68
See application file for complete search history.

(56) References Cited

U.S. PATENT DOCUMENTS

| | | |
|---|---|---|
| 5,273,598 A | 12/1993 | Higasihara et al. |
| 7,119,655 B2 | 10/2006 | Starling et al. |
| 2005/0037397 A1 | 2/2005 | Mirkin et al. |
| 2008/0305957 A1* | 12/2008 | Thisted ................ C12Q 1/6811 506/4 |
| 2017/0233726 A1* | 8/2017 | Hansen ................. C12N 15/11 506/9 |

FOREIGN PATENT DOCUMENTS

| | | |
|---|---|---|
| WO | WO2004/038037 | 5/2004 |
| WO | WO2007/084192 | 7/2007 |

OTHER PUBLICATIONS

Zhao et al. (Angew. Chem. Int. Ed. 2014, 53, 10056-10059).*

\* cited by examiner

*Primary Examiner* — Robert H Havlin
(74) *Attorney, Agent, or Firm* — Purdue Research Foundation; Liang Zeng Yan

(57) ABSTRACT

Systems, kits, and methods for detecting and quantifying proteomic activity using DNA-encoded probes are provided, where the proteomic activity may be enzymatic activity or ligand binding affinity. Such systems and methods encode quantitative proteomic activity information into DNA sequence populations and utilize DNA-linked substrates or ligands as activity probes. The systems, kits, and methods that are directed to detecting ligand affinity further include crosslinking steps to ensure the integrity of the DNA-linked ligands during purification and washing. Signal detection involves the chemical manipulation of a probe population downstream of sample exposure and application of purifying, selective pressure for desired products. Selection-induced changes in DNA abundance between the initial pool and the purified pool indicate sample activity.

23 Claims, 21 Drawing Sheets

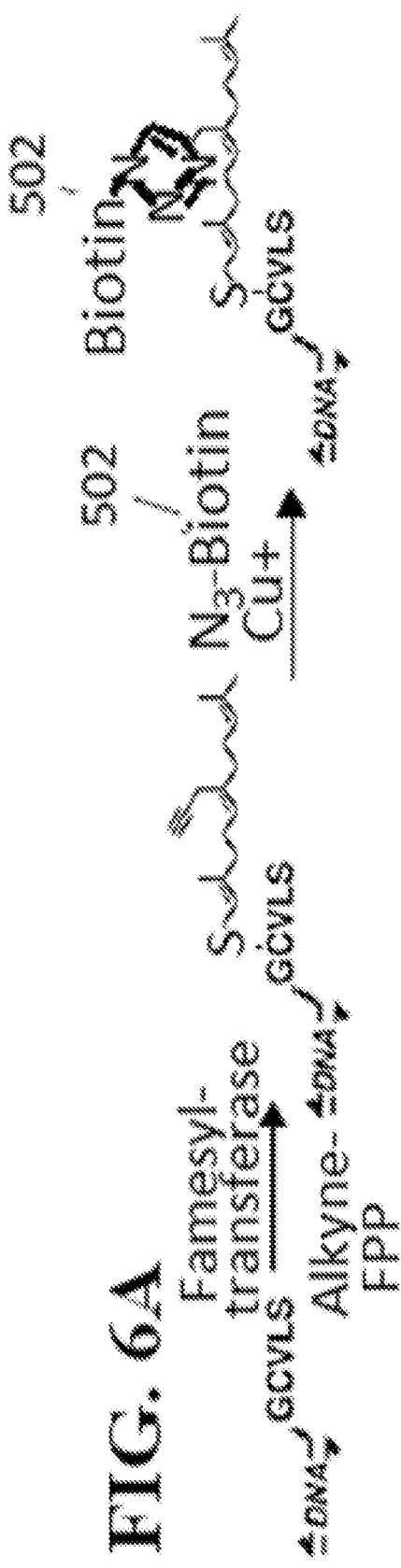
FIG. 6A
FIG. 6B

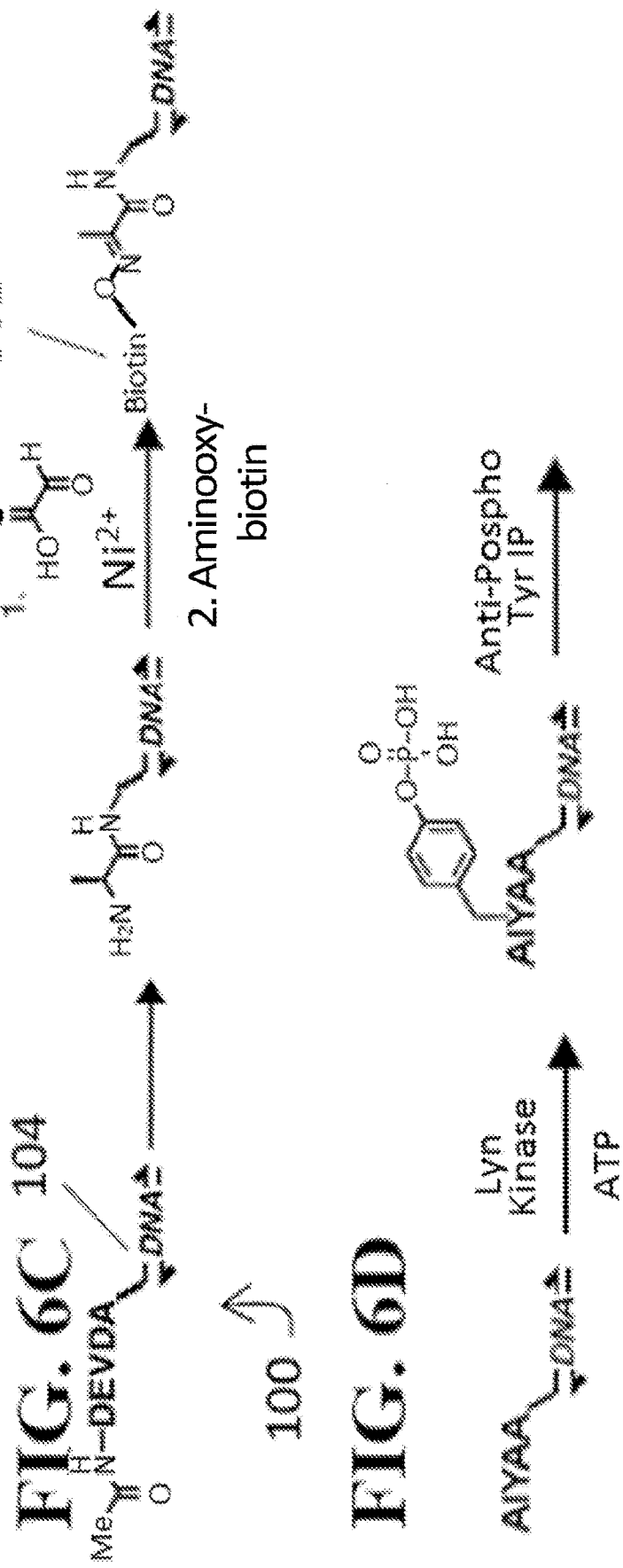

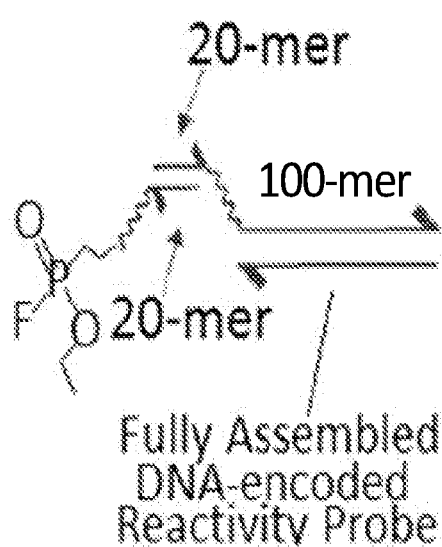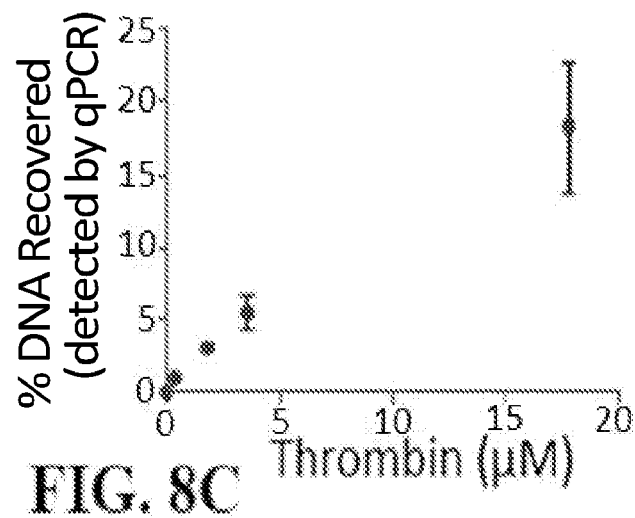
FIG. 8C
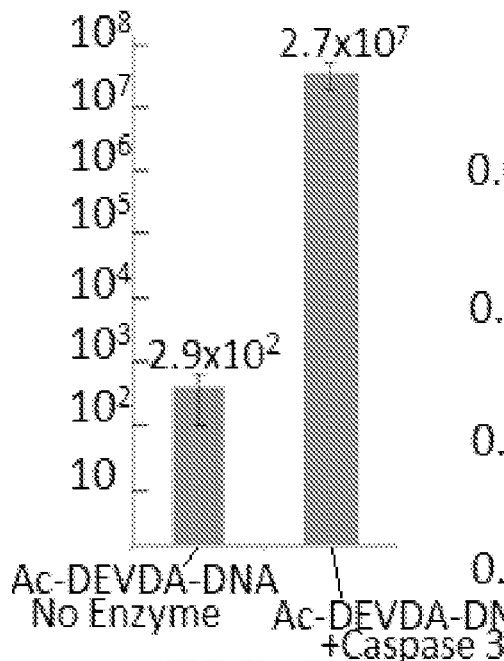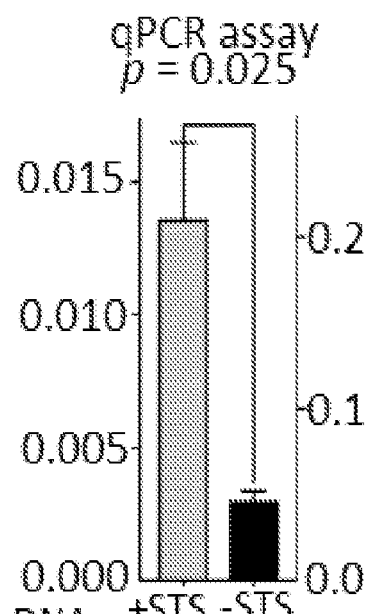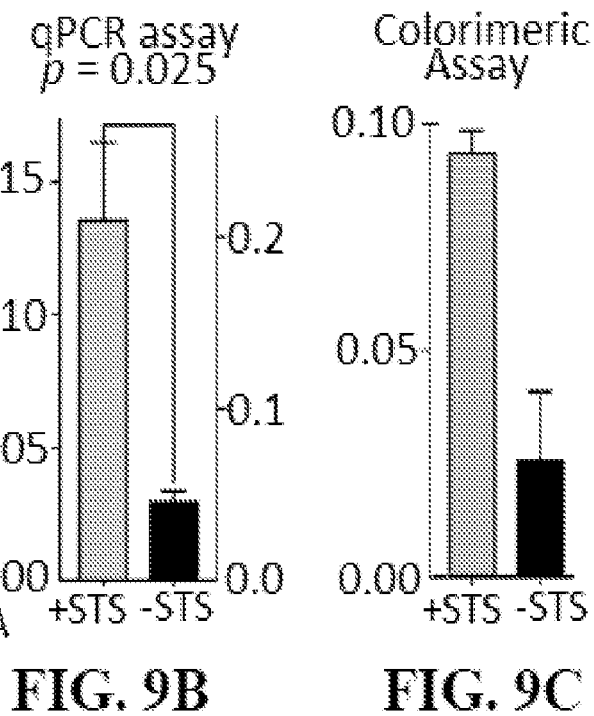
FIG. 9A  FIG. 9B  FIG. 9C

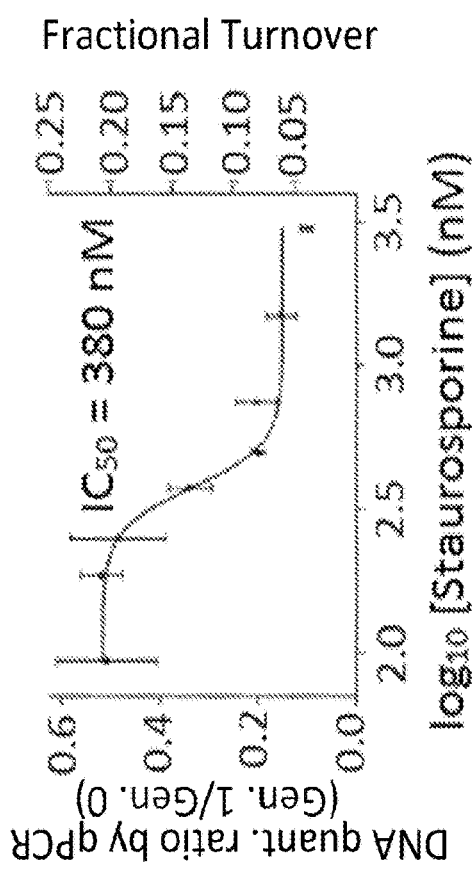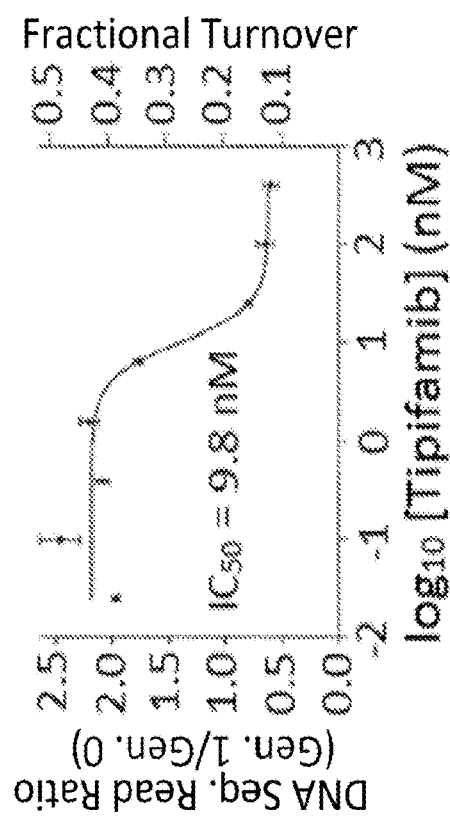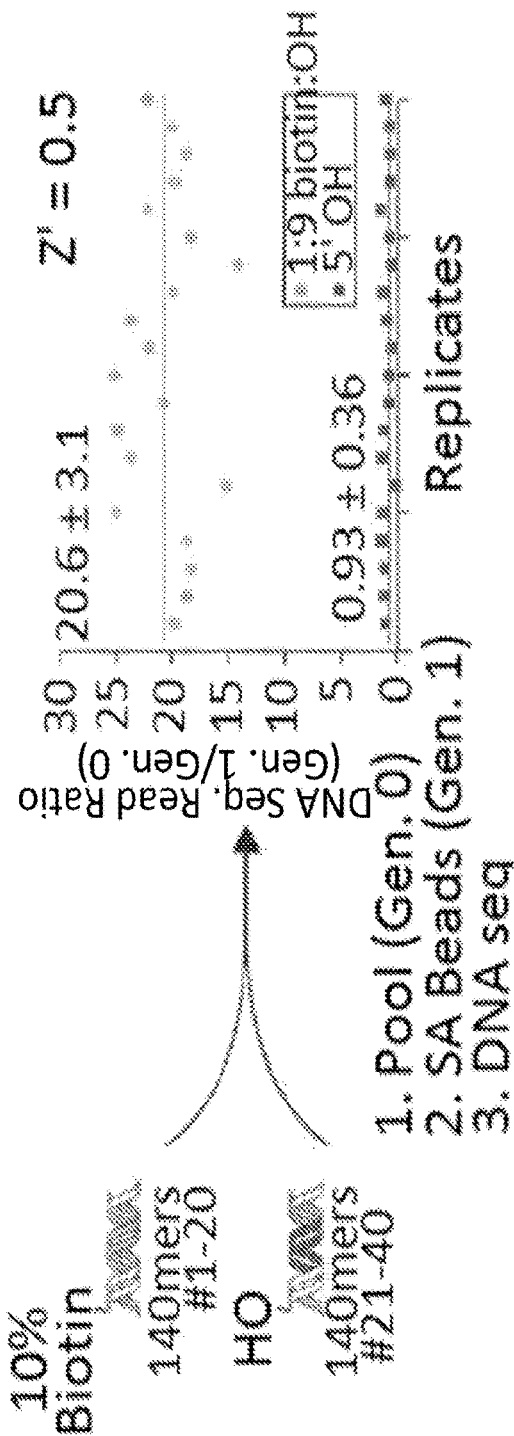
FIG. 12A
FIG. 12B
FIG. 12C

X-linking with diazirine (5)

SYSTEMS AND METHODS FOR PROTEOMIC ACTIVITY ANALYSIS USING DNA-ENCODED PROBES

CROSS-REFERENCE TO RELATED APPLICATIONS

This application is a US National Phase filing of PCT/US2016/047654, filed on Aug. 18, 2016, which claims priority to U.S. 62/206,836, filed on Aug. 18, 2015. The disclosure therein is expressly incorporated entirely by reference.

PRIORITY

This application is related to and claims the priority benefit of U.S. Provisional Patent Application Ser. No. 62/206,836 to Krusemark et al., filed Aug. 18, 2015. The content of the aforementioned priority application is hereby incorporated by reference in its entirety into this disclosure.

BACKGROUND

While advances in genomic techniques have resulted in an explosion of genomic data that has been critical to understanding cell signaling at the DNA and RNA levels, the barrier to accessing proteomic information is much greater. Conventionally, a number of approaches to assessing proteomics are available, including sensitive enzyme assays. Microfluidic devices that seek to reduce cost through miniaturization and microarrays (e.g., peptide microarrays), for example, are known. Recent developments have even included microarrays within microplates for multiplexed assays and highly multiplexed solid-phase assay formats have been developed using multicolored beads and cell sorters. Highly multiplexed solid-phase assay formats have been developed using multicolored beads and cell sorters. However, each of these approaches are often cost-prohibitive and require specialized equipment and devices, some of which are single use. Mass spectrometry is another conventional approach that has been employed as it is often highly sensitive. However, similar to microfluidic and microarray approaches, mass spectrometry requires specialized equipment and suffers from poor multiplexing capabilities. Indeed, sample multiplexing by conventional mass spectrometry is limited to about 12 samples or analytes.

Other conventional methods have attempted to address the poor multiplexing capabilities and sensitivity of standard enzyme-linked immunosorbent assay (ELISA) tests by incorporating DNA as the signal marker. Amplification of DNA allows for highly sensitive detection, approaching single molecule sensitivity. Examples of such technologies include the different variants of immuno-PCR (iPCR). iPCR is a method that combines the amplification power of polymerase chain reaction (PCR) technology with the versatility of ELISA resulting in improved conventional antigen detection sensitivity. For example, a 10-10,000-fold improvement in sensitivity can be gained by using iPCR instead of traditional ELISA techniques.

In iPCR, a linker molecule with bispecific binding affinity for DNA and protein-binding moieties (typically antibodies) is used to attach a DNA molecule (marker) specifically to an antigen-antibody complex, resulting in the formation of a specific antigen-antibody-DNA conjugate. This combines DNA-processing enzymes with the general principles of ELISA methodologies—namely, an antibody-based binding event. The attached marker DNA is then amplified by PCR with the appropriate primers. The efficacy of PCR is based on its ability to amplify a specific DNA segment and takes advantage of the intrinsic properties of the DNA molecule to be used as a substrate for signal amplification. The enormous amplification capability of PCR allows for the production of large amounts of specific DNA products, which can then be detected by various methods. Accordingly, in iPCR, after a specific antigen-antibody-DNA conjugate is formed, the conjugate is amplified by PCR and the detection of specific PCR products evidence that the marker DNA molecules are attached specifically to the targeted antigen-antibody complexes, which is indicative of the presence of an antigen.

Although iPCR is useful to determine the presence of a protein and the relative abundance thereof, it does not provide any information (qualitative or quantitative) about enzyme activity. Because protein activity information is often the most biologically relevant information and critical for many applications—particularly in the case of small molecules—iPCR's inability to detect enzyme activity significantly limits its usefulness (in diagnostic and screening assays for new therapeutics, for example). Accordingly, there is a need for a low-cost, high-throughput technique capable of providing an accurate global profile of enzymatic activity, not only the presence of the enzyme. In addition to enzymatic activity, there is also a need for such techniques to be capable of providing accurate measurements of the activity of other small molecules as well.

BRIEF SUMMARY

In at least one embodiment of the present disclosure, a kit for detecting proteomic activity in a sample is provided. The kit may comprise a population of probes and a sample comprising the target protein. Each of the probes may have a substrate specific to a target protein linked (covalently or otherwise) to a DNA construct, which comprises one or more amplifiable identification barcode regions. In certain embodiments, the barcode regions of the DNA construct comprise a unique DNA sequence detectable by DNA sequencing. The target protein is capable of reacting or binding with the substrate of a probe to convert the substrate into a product. The DNA construct encodes the product if the target protein reacts with or binds the substrate and may comprise dsDNA. The proteomic activity to be detected may comprise enzymatic activity or ligand binding affinity. In at least one embodiment, the substrate of each probe is linked to the DNA construct by a linker comprising an oligonucleotide, a modified oligonucleotide, or a primer.

The kit may comprise various probes such as substrate or covalent probes. In at least one embodiment the kit further comprises biotin or other tagging molecules. Where the substrate comprises a ligand, the resulting product comprises a DNA construct-linked ligand that is crosslinked to the target protein and attached to a reactive group and the kit further comprises a reactive group comprising an electrophilic or photoreactive group. There, the target protein can be biotinacylated or otherwise affinity tagged.

Methods for detecting proteomic activity in a sample are also provided. In at least one exemplary embodiment, a method comprises: providing a population of probes, each of the probes comprising a substrate linked to an DNA construct, the DNA construct comprising one or more amplifiable identification barcode regions and the substrate specific to a target protein; contacting the population of probes with a sample comprising a target protein in an initial pool and under conditions and for a sufficient time to allow the target protein to turnover the substrate of a probe into a product such that the DNA construct of such probe encodes the product; quenching enzyme activity within the initial pool; isolating the DNA constructs of the probes of the initial pool into a DNA pool; separating the DNA constructs of the DNA pool that encode the product to form a purified pool; quantifying the DNA constructs of the DNA pool and the DNA constructs of the purified pool; and detecting the presence or absence of a detectable signal, the detectable signal comprising identifying a change in probe frequency between the DNA pool and the purified pool. In certain embodiments, a barcode region of each DNA construct identifies a source of the sample.

In at least one embodiment, the step of quantifying the DNA of the DNA pool comprises determining a probe abundance measurement for the initial pool and a probe abundance measurement for the purified pool, and wherein the absence of the detectable signal comprises a change in the probe abundance measurements between the initial and purified pools. Still other embodiments may further comprise the steps of isolating the DNA constructs of the probes of a sample of the initial pool and isolating the DNA constructs of the probes within the purified pool, wherein the step of quantifying the DNA constructs of the initial pool and the DNA constructs of the purified pool further comprises performing a quantitative polymerase chain reaction assay on the DNA constructs of the sample of the initial pool and the DNA constructs of the purified pool.

Additionally or alternatively, the step of separating the DNA constructs of the DNA pool that encode the product to form a purified pool further comprises: reserving a small sample of the initial pool; sequencing the DNA constructs of that portion of the initial pool; and sequencing the DNA constructs of the purified pool. There, sequencing the DNA constructs may comprise parallel DNA sequencing or high-throughput DNA sequencing.

In certain embodiments, the initial pool may further comprise a population of control probes. Each control probe may comprise a control product/substrate linked to a DNA construct having one or more barcode regions. Additionally, the method may also comprise: separating, into a control pool, the DNA constructs of the DNA pool that encode a control probe, and quantifying the DNA constructs of the control pool to determine a probe abundance measurement therefore. There, this may also include quantifying the DNA constructs of the control pool, and the step of detecting the presence/absence of a detectable signal may further comprise comparing the probe abundance measurement for the control pool with a probe abundance measurement for the control probe within the initial pool to establish a baseline parameter. There, the control product of each control probe may comprise a fully cleaved peptide or a negative control. Separation of probes that comprise product-DNA conjugates and/or controls from the initial population may be performed using streptavidin magnetic beads.

Detecting the presence/absence of a detectable signal may comprise comparing the quantitative polymerase chain reaction results of the sample from both the initial and purified pools. Furthermore, a correlation exists between probe abundance change and the functional activity of the target protein a sample, where probe abundance change is determined as the abundance ratio between the probe abundance measurement of the probe in the purified pool as compared to the probe abundance measurement of the probe in the initial pool. In certain embodiments, the target protein comprises an enzyme and a low correlation between the probe abundance measurement of the initial pool and the probe abundance measurement of the purified pool is indicative of enzyme inhibition of the target protein. The proteomic function may also comprise enzymatic activity of the target protein.

Multiplexing methods are also provided. For example, the population of probes of the methods hereof may comprise at least first and second subsets of probes, each comprising a substrate specific to a target protein (e.g., a first substrate specific to a first target protein and a second substrate specific to a second target protein. In such embodiments, the step of contacting the population of probes with a sample further comprises contacting the first subset of probes with a first sample comprising the first target protein and the second subset of probes with a second sample comprising the second target protein under conditions and for sufficient time to allow the target protein to react with the respective substrate. The method may also comprise: pooling the first subset of probes/first sample with the second subset of probes/second sample to form the initial pool. There, each probe has information encoded in at least one barcode region thereof to identify its subset and/or sample.

The target protein may, without limitation, comprise a farnesyltransferase, a protein kinase, or a protease. The probes of the population may comprise either substrate probes or covalent probes. Optionally, each of the probes, target proteins, or the like may comprise an affinity tag (biotin or otherwise) or be labeled therewith (via, for example selective labeling and/or chemical biotinylation). In certain embodiments, the proteomic function to be detected comprises enzyme activity and the substrate comprises an enzyme substrate or a protein-directed covalent modifier. The linker of the DNA-encoded probe may be an oligonucleotide, a modified oligonucleotide, a primer, or the like. In exemplary embodiments, at least one of the barcode regions of the double-stranded DNA is unique (e.g., for identification purposes).

Steps for synthesizing probes are also provided, including, for example: attaching a substrate to a linker to form an oligonucleotide-substrate conjugate; and appending the substrate of the oligonucleotide-substrate conjugate to a double-stranded DNA having one or more unique amplifiable identification barcode regions for encoding the substrate. of providing a population of probes further comprises the steps of: chemically synthesizing an oligonucleotide-substrate conjugate; and hybridizing the oligonucleotide-substrate conjugate to a DNA construct. Chemically synthesizing an oligonucleotide-substrate conjugate may comprise direct peptide synthesis on amine-modified oligonucleotides or postsynthetic conjugation using copper-catalyzed azide-alkyne cycloaddition, for example.

Steps for providing a population of probes may also further comprise hybridizing an activity-based protein profiling probe to a double-stranded DNA construct comprising an accepting single-stranded DNA strand. In certain embodiments, such activity-based protein profiling probe may comprise a warhead, a specificity element, and an affinity label and, in exemplary cases, the proteomic function to be detected comprises ligand binding affinity.

Methods are also provided that comprise the steps of: providing a population of probes, each of the probes comprising a ligand linked to a DNA construct, the DNA construct comprising one or more amplifiable identification barcode regions; in an initial pool, contacting the population of probes with a sample comprising a target protein and a reactive group under conditions and for a sufficient time to allow for crosslinking of the probe to the target protein such that the DNA construct of such probe encodes the target protein; denaturing the target protein; immobilizing the target protein onto a solid support via an affinity tag coupled attached thereto; washing the crosslinked probe; isolating the DNA constructs of the probes of the initial pool into a DNA pool; separating the DNA constructs of the DNA pool that encode the target protein to form a purified pool; quantifying the DNA constructs of the DNA pool and the DNA constructs of the purified pool; and detecting the presence or absence of a detectable signal, the detectable signal comprising identifying a change in probe frequency between the DNA pool and the purified pool; wherein a small change in probe frequency is indicative of ligand binding affinity for the target protein within the sample. There, for example, the proteomic activity to be detected comprises ligand binding affinity. In some cases the reactive group is an electrophilic or photoreactive group. In other embodiments, the reactive group is selected from a group consisting of: tosyl, N-hydroxysuccinimide ester, sulfonyl fluoride, diazirine, and phenyl azide.

The ligand of each probe may be linked to the DNA construct by a single-stranded DNA tether and the reactive group may comprise a single-stranded DNA that is complimentary to the single-stranded DNA tether of the DNA construct. The DNA construct may be linked to the single-stranded DNA tether via a polyethylene glycol spacer or otherwise. Furthermore, as previously described, an affinity tag of the target protein may comprise a biotin molecule. In yet additional embodiments, the reactive group comprises a 5'-fluorescein amid modification to facilitate detection of crosslinking. Additionally or alternatively, the initial pool may further comprise a population of control probes capable of displacing the ligand of each probe from binding the target protein in furtherance of measuring ligand binding affinity (for use as a displacement assay, for example).

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIGS. 6A-6E show the selective labeling of enzyme products using a chemical biotinylation approach for farnesyltransferase (FTase) (FIG. 6A), protein kinase A (PKA) (FIG. 6B), caspase 3 enzyme products (FIG. 6C), and lyn kinase (FIG. 6D), with Alkyne-FPP=(2E,6Z)-7-Propynyl-3, 11-dimethyldodeca-2,6,10-trienyl diphosphate, synthesized and available in the art at least pursuant to Placzek et al., New Synthetic Methodology for the Construction of 7-Substituted Farnesyl Diphosphate Analogs, Org. Lett. 2011, 13 (14): 3576-3579 which is incorporated by reference herein in its entirety; ATP-γ-S=adenosine 5'-[γ-thio]triphosphate; and streptavidin purification and qPCR detection for GCVIS-DNA and FTase (FIG. 6E);

FIG. 7D shows a bar graph representative of normalized recovery of DNA-encoded probes of the present disclosure in response to indicated treatments and streptavidin affinity purification (error bars representing one standard deviation for 3-5 unique DNA constructs treated as indicated herein; same experiment as results shown in FIGS. 6E and 9A);

FIGS. 8A-8C show a schematic representation of the selective labeling of serine hydrolase, Factor Xaprotease, with a fluorophosphonate (FP) oligo probe according to an embodiment of the present disclosure (FIG. 8A); the results of immunopurification via fluorescence gel imaging of the FP oligo probe of FIG. 8A, supporting the selectivity and dependence of probe labeling as detected by SDS-PAGE (FIG. 8B); and the enzyme dependence of signal in multiplexed detection of thrombin activity using the FP oligo probe of FIG. 7A hybridized to encoding 55-mers; 15 DNA constructs were hybridized to the FP oligo probe and incubated at 5 different thrombin concentrations; samples pooled and immunopurified, and the pool subsequently analyzed by qPCR using construct specific primers (FIG. 8C);

FIGS. 9A-9C show bar graphs related to the selective biotinylation of protease product-DNA conjugates as detected by or streptavidin purification and qPCR detection (FIG. 9A) and the detection of change in caspase 3 activity in response to apoptosis induction with STS in HeLa cells using qPCR (FIG. 9B) or a colorimetric assay (FIG. 9C) of cell lysates;

FIGS. 12A-12B illustrate: the application of DNA-encoded probes for detection of enzyme inhibition and in a mock multiplexed assay, with FIGS. 12A and 12B showing the determination of $IC_{50}$ values for the FTase inhibitor tipifarnib by DNA sequencing (FIG. 12A) and for the PKA inhibitor STS by qPCR (FIG. 12B) (error bars represent one standard deviation of the signal for four unique DNA constructs at a single inhibitor concentration; and a plot representative of sequence variability for multiplexed activity detection (FIG. 12C) to mimic assay screening at 10% turnover, 20 unique constructs were prepared that were partially biotinylated (10%) and then mixed with 20 nonbiotinylated, control constructs; after streptavidin purification, sample pools were sequenced; solid lines indicate sample means;

FIG. 16B showing FAM fluorescence results of SDS-PAGE analysis from crosslinking with phenyl azide (5)—lanes 1, 7: CAII and BSA only, lanes 2, 8: non-ligand ssDNA (5'-OH-ssDNA), lanes 3, 9: 1 μM GL-CBS-ssDNA, lanes 6, 12: no CAII; lanes 1-6: 10 μM CAII and 10 μM BSA, lanes 7-12: 1 μM CAII and 1 μM BSA; and FIG. 16C showing FAM fluorescence results of SDS-PAGE analysis from crosslinking with sulfonyl fluoride (3)—lane assignments same as listed for FIG. 16B.

Figure 1:
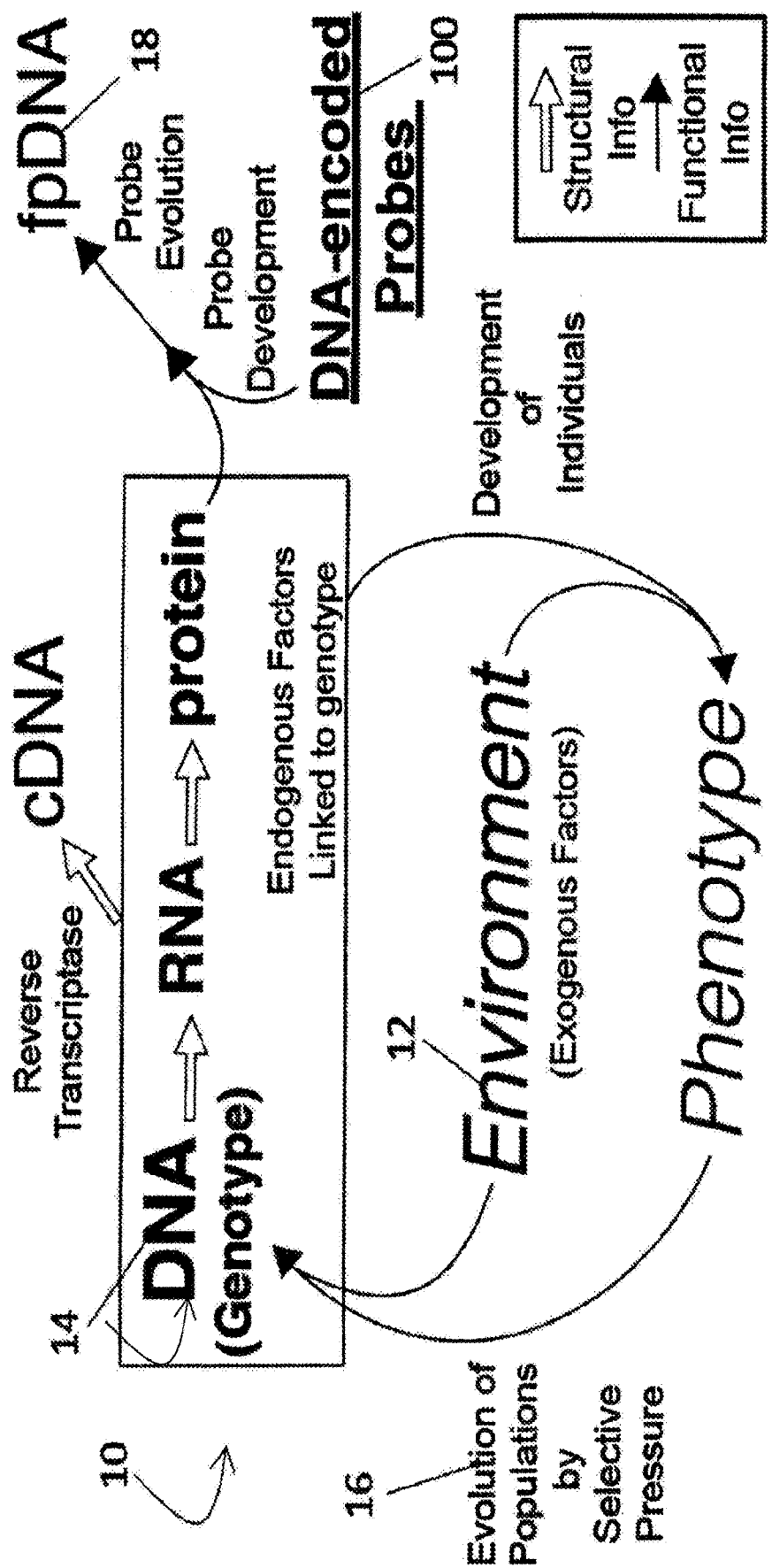
FIG. 1 shows a schematic view of the flow of functional information through evolution as observed in nature.

The flow charts and schematics depicted in the figures are representative in nature and actual embodiments of the systems and methods hereof may include further features or steps not shown in the drawings. The exemplification set out herein illustrates an embodiment of the systems and methods, in one form, and such exemplifications are not to be construed as limiting the scope of the invention in any manner. An overview of the features, functions and/or configurations of the components depicted in the various figures will now be presented. It will be appreciated that not all of the features of the components of the figures are necessarily described. Some of these non-discussed features, as well as discussed features, are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings and specific language will be used to describe the same. It will nevertheless be understood that no limitation of scope is intended by the description of these embodiments. On the contrary, many modifications and other embodiments of the technology described herein will come to mind to one of skill in the art to which the present disclosure pertains having the benefit of the teachings presented in the present descriptions and associated figures. Therefore, it is understood that this disclosure covers any such alternatives, modifications, and equivalents as may be included within the spirit and scope of this application as defined by the specification and appended claims. As previously noted, while this technology may be illustrated and described in one or more preferred embodiments, the compositions, systems and methods hereof may comprise many different configurations, forms, materials, and accessories.

In the following description, numerous specific details are set forth in order to provide a thorough understanding of the present disclosure. Particular examples may be implemented without some or all of these specific details and it is to be understood that this disclosure is not limited to particular biological systems, which can, of course, vary.

Furthermore, wherever feasible and convenient, like reference numerals are used in the figures and the description to refer to the same or like parts or steps. The drawings are in a simplified form and not to precise scale. It is understood that the disclosure is presented in this manner merely for explanatory purposes and the principles and embodiments described herein may be applied to devices and/or system components that have dimensions/configurations other than as specifically described herein. Indeed, it is expressly contemplated that the size and shapes of the composition and system components of the present disclosure may be tailored in furtherance of the desired application thereof. Unless defined otherwise, all technical and scientific terms used herein have the same meaning as commonly understood by one of skill in the relevant arts. Although any methods and materials similar to or equivalent to those described herein can be used in the practice or testing of the subject of the present application, the preferred methods and materials are described herein. Additionally, as used in this specification and the appended claims, the singular forms "a", "an" and "the" include plural referents unless the content clearly dictates otherwise. Furthermore, unless specifically stated otherwise, the term "about" refers to a range of values plus or minus 10% for percentages and plus or minus 1.0 unit for unit values, for example, about 1.0 refers to a range of values from 0.9 to 1.1.

A "subject" or "patient," as used herein, is a mammal, preferably a human, but can also be an animal who is being tested for biomarker expression. A "marker" or "biomarker" as the terms are used herein may be described as being differentially expressed when the level of expression in a subject who is experiencing or likely to experience a disease condition is significantly different from that of a subject or sample taken from a subject not experiencing, or not likely to experience, the disease condition. A differentially expressed marker may be overexpressed or underexpressed as compared to the expression level of a normal or control sample or subjects' baseline. The increase or decrease, or quantification of the markers in a biological sample may be determined by any of the several methods known in the art for measuring the presence and/or relative abundance of a gene product or transcript. The level of markers may be determined as an absolute value, or relative to a baseline value, and the level of the subject's markers compared to a cutoff index (e.g., a non-rejection cutoff index). Alternatively, the relative abundance of the marker or markers may be determined relative to a control, which may be a clinically normal subject (e.g., one who has not received an allograft) or may be an allograft recipient that has not previously demonstrated active rejection.

A "profile" or "assay" is a set of one or more markers and their presence, absence, and/or relative level or abundance (relative to one or more controls). For example, an enzymatic assay is a dataset of the presence, absence, relative level or abundance of an enzyme present within a sample. A genomic or nucleic acid profile is a dataset of the presence, absence, relative level or abundance of expressed nucleic acids (e.g., DNA, transcripts, mRNA, or the like). "Down-regulation" or "down-regulated" may be used interchangeably and refer to a decrease in the level of a marker, such as a gene, nucleic acid, metabolite, transcript, protein, or polypeptide. "Up-regulation" or "up-regulated" may also be used interchangeably and refer to an increase in the level of a marker, such as a gene, nucleic acid, metabolite, transcript, protein, or polypeptide. Also, a pathway, such as a signal transduction or metabolic pathway may be up- or down-regulated.

As used herein, the term "target" when used to refer to a protein or enzyme is used to refer to any chemical, biochemical or biological species or compound that is known or referred to in the art as a protein or enzyme. A target enzyme includes those compounds having proteolytic, catalytic or enzymatic activity. A target enzyme includes those compounds able to modify a substrate so as to alter or change the substrate's chemical structure or apparent structure or activity. A target protein includes those compounds to which a ligand or other small molecule may bind and/or have an affinity for binding. The term "substrate" is used to refer to any chemical, biochemical, or biological species or compound that complexes with, reacts with, is capable of being modified by, or otherwise interacts with an enzyme having bioactivity. As used herein, the terms "fluorogenic substrate" and "fluorophore" may be used interchangeably to describe a substrate that is hydrolyzed by or otherwise reacted with a target enzyme upon contact therewith, producing a complex, product or other derivative thereof which liberates fluorescence upon excitation by a suitable light source. As used herein, the term "primer" means a strand of short nucleic acid sequences that serves as a starting point for DNA synthesis and comprises a free 3'-end.

The term "probe" means a nucleic acid fragment, such as RNA or DNA, that comprises a protein substrate, ligand/small molecule, a reactive group (i.e. warhead) and/or a tag, as is further described in detail herein. The reactive group may contain a specifically designed electrophile or photoreactive group that becomes covalently or otherwise linked to a nucleophilic residue in the active site of an active enzyme. Certain reactive groups can enhance selectivity and the tag can be a reporter (such as a fluorophore) or an affinity label (e.g., biotin) as described herein. The probes of the present disclosure can be chemically synthesized as described herein and using other methods known in the art.

The terms "multiplex" and "multiplex assay" as used herein mean a type of assay that simultaneously measures multiple analytes in a single run or cycle of the assay. The term "high-throughput" means a technique that is capable of rapidly processing multiple specimens in an automated fashion—either through massive parallelization of assays, automating a procedure, or through other means known in the art—to identify active compounds, antibodies, or genes that module a particular biomolecular pathway. The term "kit" refers to a combination of reagents and other materials. As used herein, an "instructional material" includes a publication, a recording, a diagram, or any other medium of expression that can be used to communicate the manner in which the compounds described herein are used in practicing the assay and/or methods of the present disclosure.

Of significance of the present disclosure, at least in part, is not the particular methods used for exposure, purification and/or selective pressure, and/or detecting/quantifying the DNA and/or abundance of DNA in a resulting purified pool, but what the overall methods and abundance quantifications are used to achieve and detect. There are many methods that may be used to selectively purify a probe population based on phenotype or to amplify and/or quantify DNA. One of skill in the art, when provided with the novel concepts, systems, and methods to be identified, will be capable of selecting the appropriate assay (e.g., streptavidin magnetic beads for separating products from substrates, a quantitative PCR-based assay for nucleic acid markers, etc.) for performing the methods disclosed herein.

Embodiments of the present disclosure provide various systems, methods and techniques relating to DNA-encoded probes for detecting and/or quantifying proteomic activity. Proteomic activity may comprise a variety of activities and conditions, but in exemplary embodiments of the present disclosure comprises enzymatic activity or ligand binding affinity. The DNA-encoded probes hereof allow for the low-cost, high-throughput profiling of proteomic activity in samples using DNA sequence analysis, and also exhibit extensive multiplexing capabilities. In addition to the inventive DNA-encoded probes described herein, the present disclosure also provides methods and techniques for the detection of activity and for the detection and diagnosis of disease conditions based on the use of such inventive probes. This is significant because the probes and methods described allow for the quantification of proteomic activities of metabolic and signaling pathways (i.e. proteomic functional information) in complex samples, which enables system-wide profiling of the functional biochemical status of biological samples at a sensitivity and breadth that was heretofore not possible using conventional modalities. Assay kits are also provided that comprise one or more reagents described herein for performing the inventive methods hereof.

Conceptual Overview.

In natural selection, nature provides a mechanism through which exogenous information is encoded within DNA sequences. A flow-chart generally representative of such mechanism is shown in FIG. 1. The function of all biological molecules within their environment 12 is assessed through the process of natural selection 10 and that information is collectively contained within the genomes (DNA sequences 14) of a population. Through generations of selective pressure 16, the frequency of DNA alleles encoding molecules 12 of greater function increases relative to those alleles encoding molecules 12 of poorer function. In sum, selection-induced allele frequency changes in a population encode the relative function of alleles within their environment (i.e. exogenous factors 12).

DNA is the central information storage molecule of biology and powerful tools exist to read, write, and manipulate DNA-encoded information. Both enzymes from nature (polymerases, restriction enzymes, recombinases, and the like) and man-made technologies (DNA synthesis chemistry, DNA sequencers, thermocyclers, etc.) have made information encoded in DNA highly accessible. The novel systems, methods, and techniques hereof leverage the power of these techniques to uniquely transduce nongenomic information into DNA sequences and measure and/or quantify such information to determine proteomic function.

To date, few approaches exist that use DNA directly to facilitate proteome characterization by protein detection. By and large, these are variants of immuno-PCR (iPCR). In such approaches, protein-binding moieties (typically antibodies) are covalently conjugated to DNA to enable sensitive detection by DNA amplification. The most notable extension of this method is the proximity ligation assay (PLA) and its proximity extension assay (PEA) variant. These approaches have demonstrated remarkable properties—for example, PEAs have demonstrated lower limits of detection between about 0.1 and about 1 fM for several analytes, which is roughly 1000-fold more sensitive than conventional ELISAs, with a 5-log dynamic range using very small (1 μl) sample volumes. In addition, utilization of the information encoding capacity of DNA has enabled these assays to be extensively multiplexed. For example, similar assays using slow off-rate, modified RNA aptamers (SOMAmers) have been employed in the simultaneous quantitation of 813 proteins.

However, unlike conventional modalities, the novel systems and methods hereof utilize DNA-assisted proteomic assays to directly detect protein activity (as opposed to solely the presence thereof) with extremely high sensitivity. Some non-limiting examples of protein activity may include ligand binding affinity or reactivity. This is important because, unlike conventional methods, the techniques of the present disclosure are not limited by inhibitory proteins or if there are not antibodies available for a particular protein, and also directly detect such activity rather than relying on a downstream affect that renders less accurate results. In at least one exemplary embodiment of the present disclosure, such systems and methods report proteomic functional activity on a proteome-wide scale by encoding the same in a DNA sequence. This in vitro scheme mimics the underlying flow of functional information through evolution as observed in nature (e.g., natural selection 10).

Systems and Methods.

Figure 2:
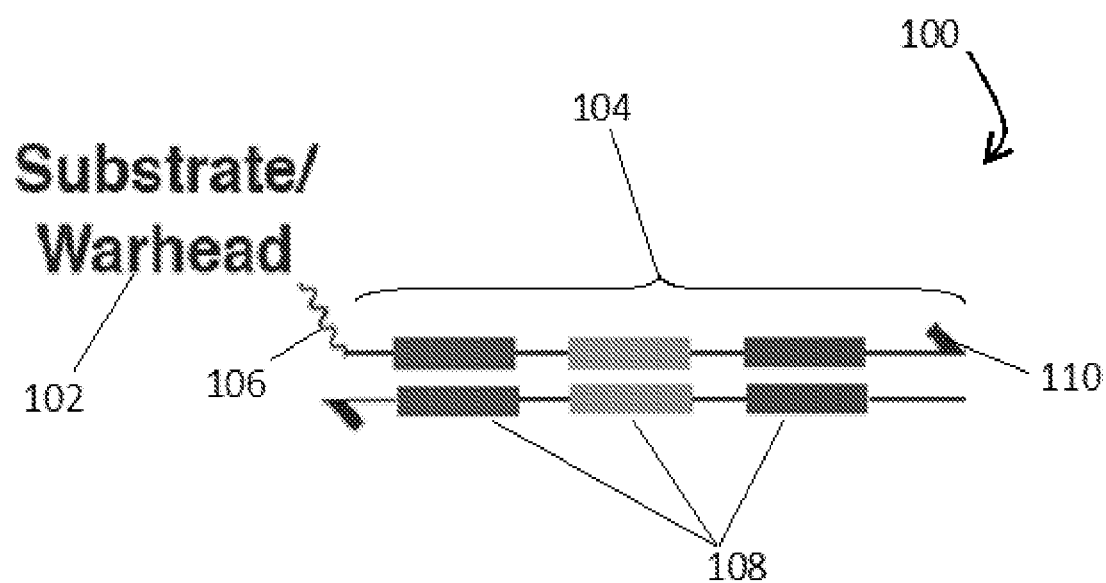
FIG. 2 shows a schematic view of a proteomic probe according to the present disclosure.
Figure 3A:
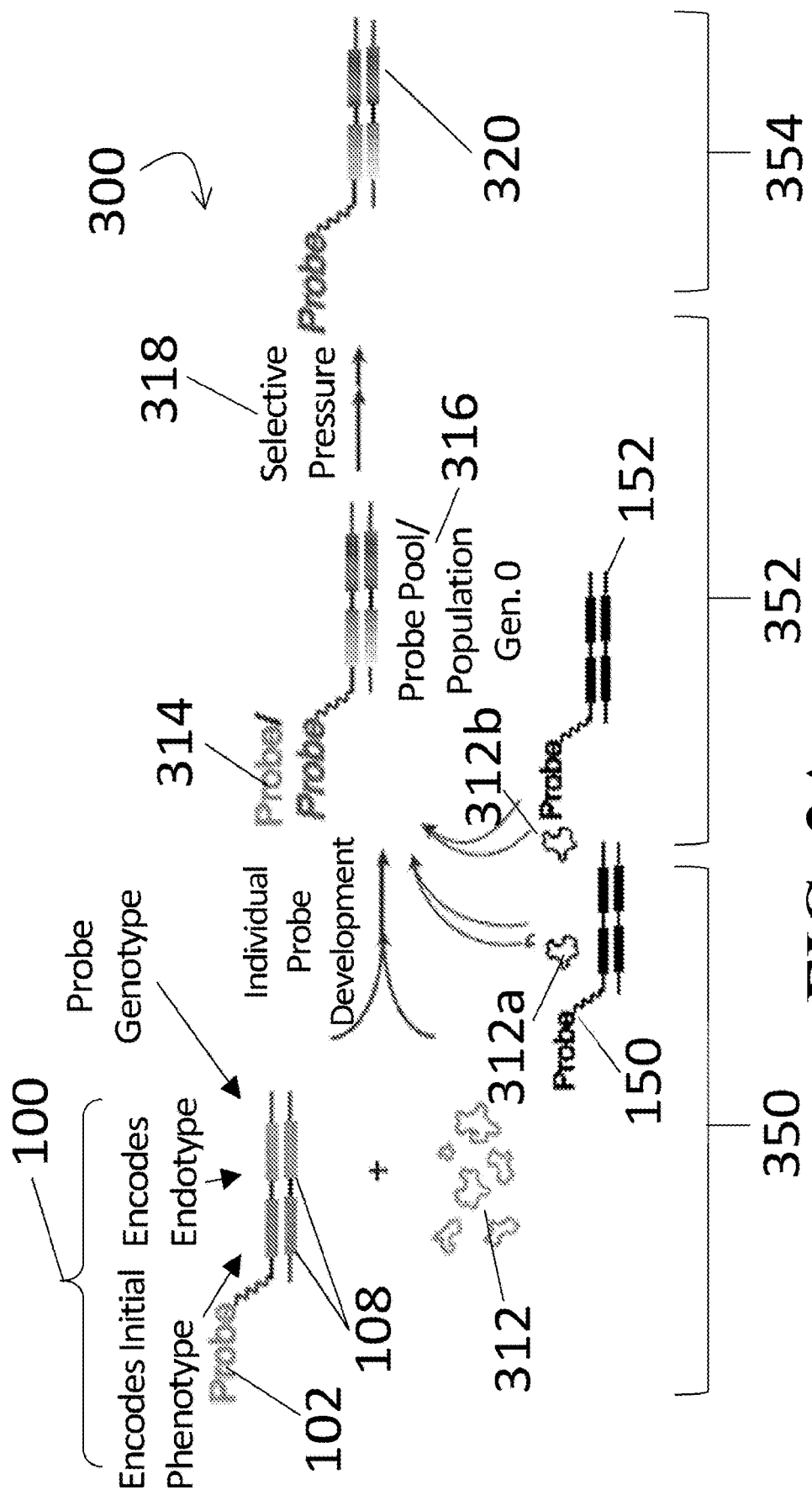
FIGS. 3A-3B show schematics of a method of the present disclosure for detecting proteomic activity using the DNA-encoded proteomic probe of FIG. 2.
Figure 3B:
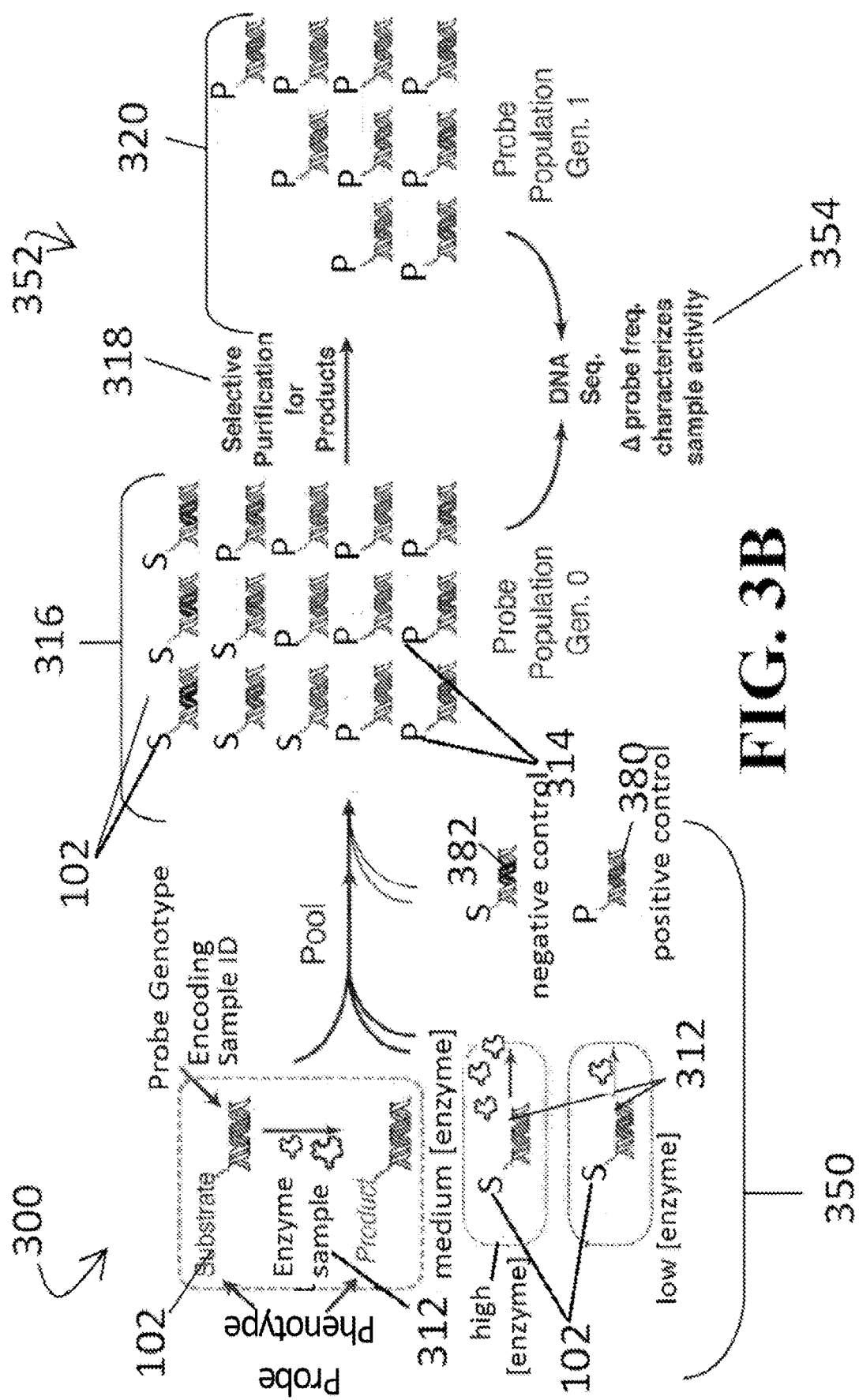

Now referring to FIGS. 2 and 3A-3B, at least one exemplary embodiment of a DNA-encoded probe 100 (FIG. 2) and a method 300 for selection-based sensing using DNA-encoded probes 100 (FIGS. 3A and 3B) are shown. Generally, the method 300 links probe molecules 102 to DNA barcodes 104 (step 350—preparing the DNA-encoded probe 100 and exposure step) and leverages proteomic samples 312 through purification and/or selective pressure 318 (step 352—purifying/selection step) to affect phenotypic changes to populations of DNA-encoded probes 316 and, thus, enrich for reacted probes. In other words, where there is the targeted proteomic activity, the protein samples affect phenotypic changes in the probes 100 which can be read through barcodes and thus influence survivability of a selection. Accordingly, when selective pressure 318 is applied to the probe population 100 (using, for example, streptavidin magnetic beads or as otherwise described herein or known in the art), a change in probe (allele) frequency in the purified pool is indicative of proteomic function within the proteomic samples (i.e. a compound—ligand, small molecule, protein, enzyme, etc.—has bound to the DNA-encoded probe 100 and the "product" has been encoded in the DNA construct 104). A detected change in probe frequency or probe abundance of the probe population, as monitored by quantitative PCR, DNA sequencing, or any other applicable process now known or hereinafter developed for specific quantification of DNA and/or nucleic acids, then serves as the assay signal (step 354—comparison step). In other words, the correlation between the quantitative or relative DNA abundance reads of the between the initial pool of probes and the purified pool of probes (i.e. those that reacted) is directly related to the occurrence of the targeted proteomic activity. For example, not taking into account variations related to selection efficiency and signal detection for the sake of simplicity, if the results indicate a much lower abundance of probes in the purified pool as compared to the initial pool, this is indicative of a low amount of the targeted proteomic activity and vice versa. As such, the proteomic samples 312 play the role of environment 12 in natural selection 10 and the DNA-encoded probes 100 equate with the resulting genetically-encoded entities. In addition to detecting proteomic function, the inventive systems and methods hereof also allow for the storage and access of proteomic function information within a DNA library (e.g., a functional proteomic DNA library (fpDNA 18 of FIG. 1)). Indeed, the biomimetic, selection-based sensing approach described herein can accurately identify proteomic information using DNA-linked activity probes and achieve system-wide proteomic profiling through the use of a fpDNA library.

Each DNA-encoded probe 100 comprises a specific substrate or warhead 102 linked to a DNA scaffold 104 (probe genotype) by a linker 106. In at least one exemplary embodiment, the substrate 102 is specifically selected to sense a particular activity or condition within an environment. In such cases, the DNA 104 encodes the identity of a particular sample 312 to which the probe 100 is exposed. The substrate 102 may comprise an enzyme substrate, a protein-directed covalent modifier, or the like. Furthermore, the substrate 102 may comprise a ligand or synthetic small molecule (for example where the probe 100 is intended to detect small molecule binding affinity). For the avoidance of doubt, as used herein, the term "substrate 102" means and includes a peptide or other substrate, a warhead, a ligand, and other small molecules unless otherwise noted. Likewise, the sample 312 may comprise proteins, enzymes, or the like—generally, any targeted compound. Specific embodiments of various DNA-encoded probes 100 that may be used in method 300 are described in additional detail below.

The linker 106 of the DNA-encoded probe 100 may comprise any linker known in the art or hereinafter developed such as an oligonucleotide, a modified oligonucleotide, a primer, or the like. In at least one embodiment, the linker 106 comprises a 5' linker. The substrate 102/linker 106 conjugate is then put on the unique barcoded DNA scaffold 104. The DNA scaffold 104 comprises one or more DNA barcode regions 108 for encoding the substrate 102 identification/sample identification and double stranded DNA 110 for detection purposes. In other words, the DNA barcode region(s) 108 serve to identify both initial probe 100 phenotype and the probe environment. As such, the DNA barcode region(s) 108 may comprise any barcode 108 (or combinations thereof) desired, provided such barcode region(s) 108 are distinguishable from the barcode regions of any control samples. Indeed, there are no sequence dependencies with respect to the turnover and/or purification steps of method 300.

Once the DNA-encoded probe 100 is formed, a population of the DNA-encoded probes 100 is mixed with a sample 312 to create an initial pool 316. The sample 312 may comprise one or more proteins, substrates, and/or other substances and, in most cases, comprises at least a particular proteomic compound or enzyme that the probe 100 is designed to detect. In some cases, where there is proteomic or other activity present within the initial pool 316 that the probe 100 is designed to detect, exposure converts the probe 100 phenotype from substrate 102 into product 314 (step 350). Alternatively, where the method 300 is directed to detecting ligand binding affinity, exposure may result in the probe 100 binding with a targeted protein (and other cross-linking steps described in additional detail below), which is likewise encoded on the DNA construct 104 and alters the phenotype.

In the interest of facilitating a clear understanding of the present disclosure, the focus will now shift to enzymatic applications, with ligand and small molecule binding affinity assays described thereafter. For the avoidance of doubt, the underlying concepts of these variant applications remain the same unless otherwise expressly noted.

Again referring to FIGS. 3A and 3B, where a substrate 102 of a probe 100 comprises an enzymatic substrate and the proteomic samples 312 within a pool 316 comprise the appropriate active enzyme samples, whereby DNA sequences within the probes 100 encode the identity of the enzyme samples. Enzyme substrates of the probes 100 will react with the active enzymes in the proteomic samples 312. This reaction turns over the enzymatic substrates 102 of the probes 100 into products 314, thereby potentially altering the phenotype of the probe 100 from substrate 102 to product 314. The extent of the reaction is proportional to the amount of active enzyme present.

After allowing a sufficient amount of time to pass (i.e. sample exposure), enzyme activity is quenched and the probes are pooled into a probe population 316 (see pool 316 of FIG. 3B comprising both "reacted" DNA-encoded probes 100 comprising product 314 and "unreacted" DNA-encoded probes 100 comprising substrate 102). Pool 316 is then subjected to a purifying selection for product 314 probes (step 352). When selective pressure 318 for the altered phenotype is applied to the probe population 316 at step 352, a purified population 320 of the initial probe population 3016 remains (see FIG. 3B). In at least one embodiment, the purification of enzyme product-DNA conjugates uses streptavidin magnetic beads to apply selective pressure on the probe population 316; however, it will be noted that any appropriate technique may be used to purify/select out the desired product-DNA conjugates. Furthermore, in certain embodiments, DNA may be chemically or enzymatically treated and subsequently isolated from the initial and purified probe populations 316, 320 prior to the application of selective pressure 318 or other purification modalities at step 352.

At step 354, the resulting change in the quantitative or relative abundance of probes 100 between the initial pool 316 (pre-purified) and the purified population 320 is detected by DNA sequence analysis and/or quantitative PCR (qPCR) and the change in probe frequency is determined. The change in probe frequency between the populations 316, 320 is indicative of the targeted proteomic activity of the sample 312 and thus allows for the quantification of proteomic function. A detectable change in probe frequency within the population quantifies the enzymatic activity of the samples. Indeed, if the abundance of probes has remained relatively constant (or only slightly decreased) between the purified and initial pools, this indicates that the probes 100 have reacted with (i.e. "sensed") the targeted moiety or condition (i.e. proteomic function) within the proteomic samples 312 that the probes 100 were designed to detect. In this manner, the method 300 allows for the direct assessment of sample proteomic activity—not just the presence of enzymes (or targeted moieties) as with conventional methods.

Furthermore, in at least one exemplary embodiment, the initial (pre-purified) DNA pool 316 is sequenced, and a sample of DNA from the purified population 320 is sequenced to identify the various samples, reagents, etc. within a pool. The results of these sequencing assays are then compared with respect to the abundance of the DNA present within each sample, with a higher relative amount of DNA (i.e. the DNA present within the purified pool 320 selected on the basis of being linked to a product 314 and, thus, having undergone enzymatic activity) indicative of high enzymatic activity. Additionally or alternatively, a change in frequency of the barcodes 108 (alleles) of the DNA construct 104 is also indicative of proteomic function. In this manner, the method 300 allows for the direct assessment of sample proteomic activity—not just the presence of enzymes (or targeted moieties) as with conventional methods.

The method 300 hereof has a number of advantages in throughput, sensitivity, and sample multiplexing. Primarily, performing the probe manipulations, such as covalent modifications and selective purifications (step 352), on a probe pool 316 comprising several samples greatly facilitates accuracy of the method 300 and performing numerous assays concurrently. As shown in FIG. 3B, in addition to the DNA-encoded probe 100 and the proteomic samples 312, the pool 316 may comprise appropriate controls with identifying DNA barcodes 108 to normalize the results. For example, in at least one embodiment of the method 300 comprising a protease substrate assay, a DNA construct 380 containing a fully cleaved peptide product may be doped into the pool 316. The recovery of a particular probe 100 relative to a control construct 380 allows for the accurate determination of fractional turnover and a quantitative measurement of enzyme activity (e.g., helps determine background and normalize signal strength variations related to, for example, the amount of enzyme within the sample). While this DNA construct 380 control is a positive control, variations of the method 300 may additionally or alternatively utilize negative controls—for example, DNA construct 382 containing a substrate or other molecule that is not active with the target.

Additionally, multiple DNA-encoded probes with varied phenotypes and environments 150, 152 may be mixed into the same probe population 316 as desired, thus allowing for multiple enzyme targets, samples, and/or several enzymatic activities to be concurrently assessed in a single high through-put DNA analysis. Indeed, by utilizing a DNA encoding approach, the method 300 allows for highly multiplexed activity detection from multiple cell lysate samples, which is outside the capability of conventional assays (e.g., fluorescent and luminescence-based assays and ELISAs). While the method 300 is described in connection with probe 100, it will be appreciated that this is done solely for the sake of providing a clear disclosure and is not intended to be limiting. Indeed, the steps of method 300 and its underlying concepts equally apply to DNA-encoded probes 150, 152 as is herein described in connection with DNA-encoded probe 100.

Figure 4:
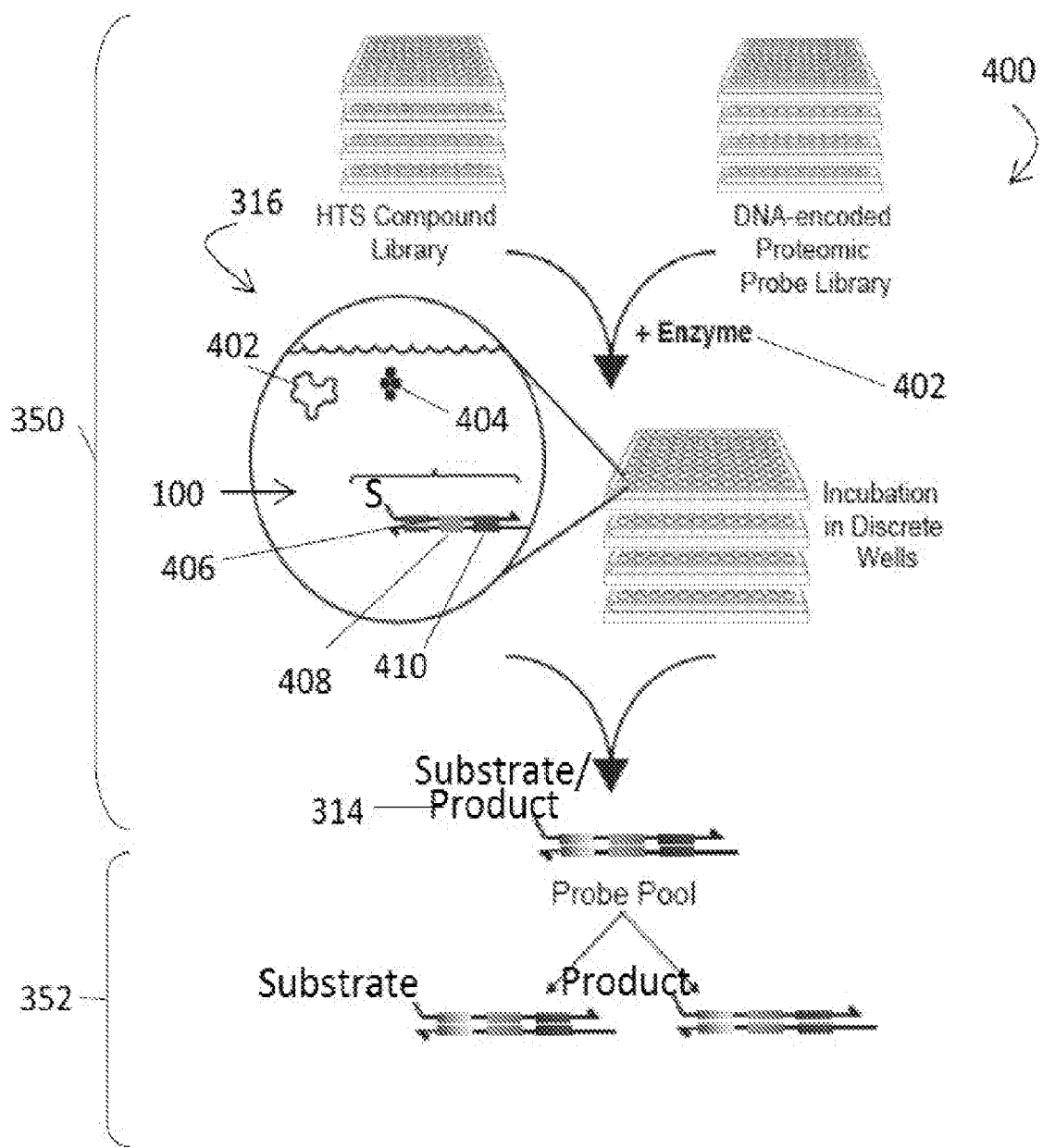
FIG. 4 shows a depiction of the method of FIGS. 3A/3B as applied to HTS.

FIG. 4 illustrates a graphical depiction of steps 350 and 352 of a method 400, which is at least one embodiment of method 300 as applied to DNA encoding of small molecule function in a high-throughput screening (HTS) application. Note that while step 354 is not shown in FIG. 4, this omission is not intended to be limiting and it is omitted only for the sake of providing a concise disclosure. Here, method 400 comprises combining a HTS library, a DNA-encoded proteomic probe library and a targeted enzyme 402 into an initial probe pool 316 and allowing each pool 316 to incubate in a discrete well (exposure portion of step 350). As shown in FIG. 4, the enzyme 402, the HTS small molecule 404, and the DNA-encoded probe 100 (comprising substrate 102) are all present within each well. Furthermore, each well of the plate may comprise a probe 100 comprising different DNA barcodes 108; in at least one exemplary embodiment, the various barcodes 108 may be designed/selected to reflect particular information—for example, the DNA barcode 406 may correspond with a plate number, DNA barcode 408 may reflect a column number, and DNA barcode 410 may reflect a row number. Following a determined amount of time to allow the substrates 102 can turn over into products 314, the enzymes 402 are denatured, and all wells are pooled to form initial probe pool 316. The DNA 104 from the probe pool 316 is then isolated. At step 352, the resulting DNA pool is subjected to purifying selection and enzymatic activity is assessed through DNA quantitation. The DNA barcodes 108 of each "reacted" or product 314 probe will be encoded with additional information related to the appropriate enzyme 402, whereas the "nonreacted" substrate 102 probes 100 will comprise the data initially encoded by the barcodes 108. In each case, however, the DNA allows for a user to not only accurately identify enzymatic activity between multiple different enzymes and samples, but also to accurately identify the plate, column, and well (for example) from which each DNA sample originated. Furthermore, as previously described, abundance measurements and a resulting change in probe frequency within a population will be assessed to quantify the enzymatic activity in the samples.

Kits.

Performance of the methods 300, 400, 1300 (below) described herein can be facilitated by providing necessary materials in kit form. Such a kit may comprise a population of probes 100 (or the components thereof if not previously synthesized), a sample comprising a target protein and a ligand or other small molecule (described in connection with method 1300 below). Additionally, kits may comprise controls (positive and/or negative) and any other reagents necessary for performing the methods hereof. The contents of the kit may vary depending on the determination(s) sought to be made and, for example, may contain one or more aliquots of various reagents. There may also be included in the kit on or more vessels useable for mixing or dispensing assay reagents, as well as instructional material for proper performance of the methods 300, 400, 1300 hereof.

Probes.

Figure 5A:
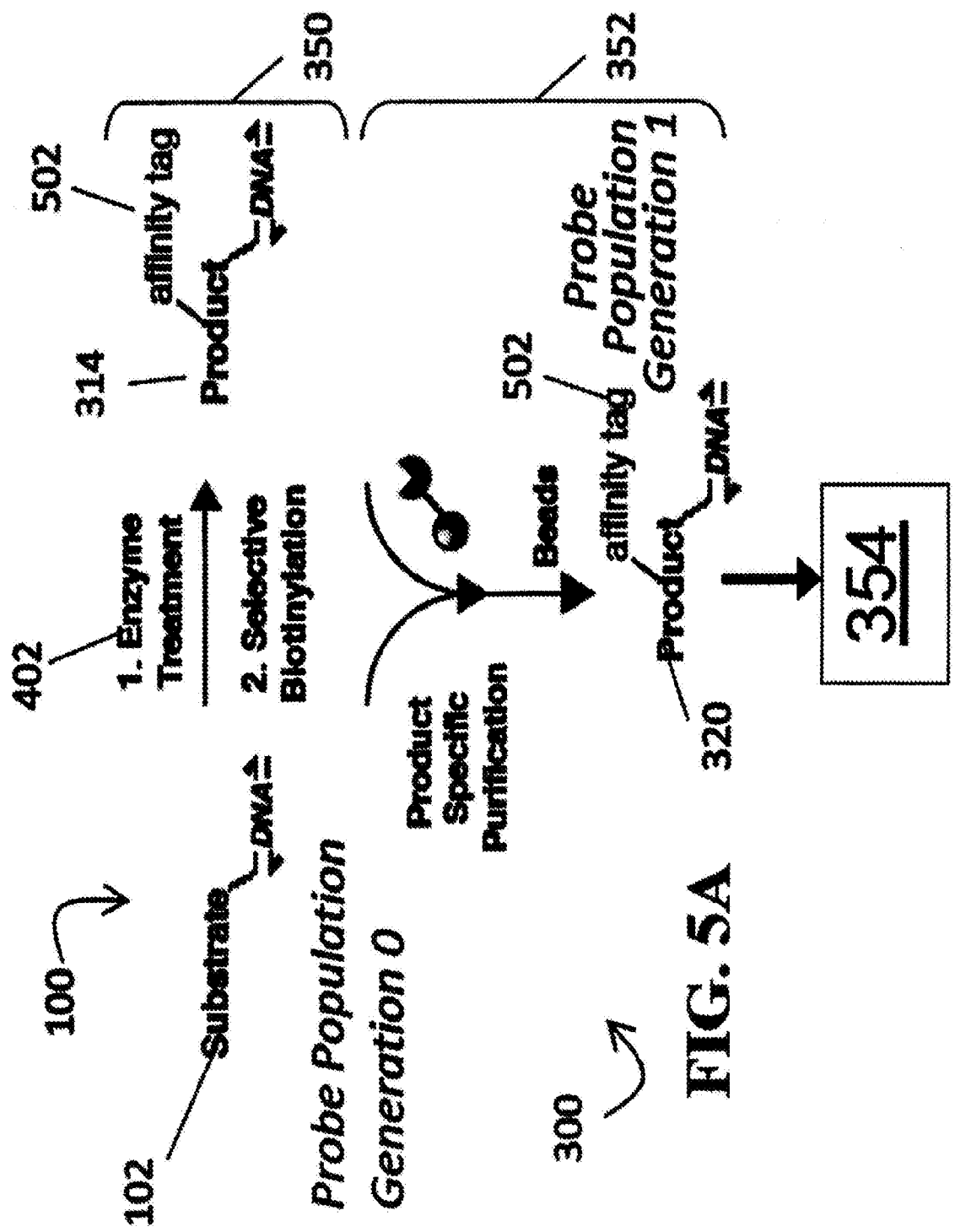
FIGS. 5A-5B show flow charts depicting the path of: 1) a substrate-based enzyme activity probe of the present disclosure through a method for detecting and quantifying proteomic activity of the present disclosure (FIG. 5A); and 2) a covalently modifying proteomic probe of the present disclosure through a method for detecting and quantifying proteomic activity according to the present disclosure (FIG. 5B)
Figure 5B:
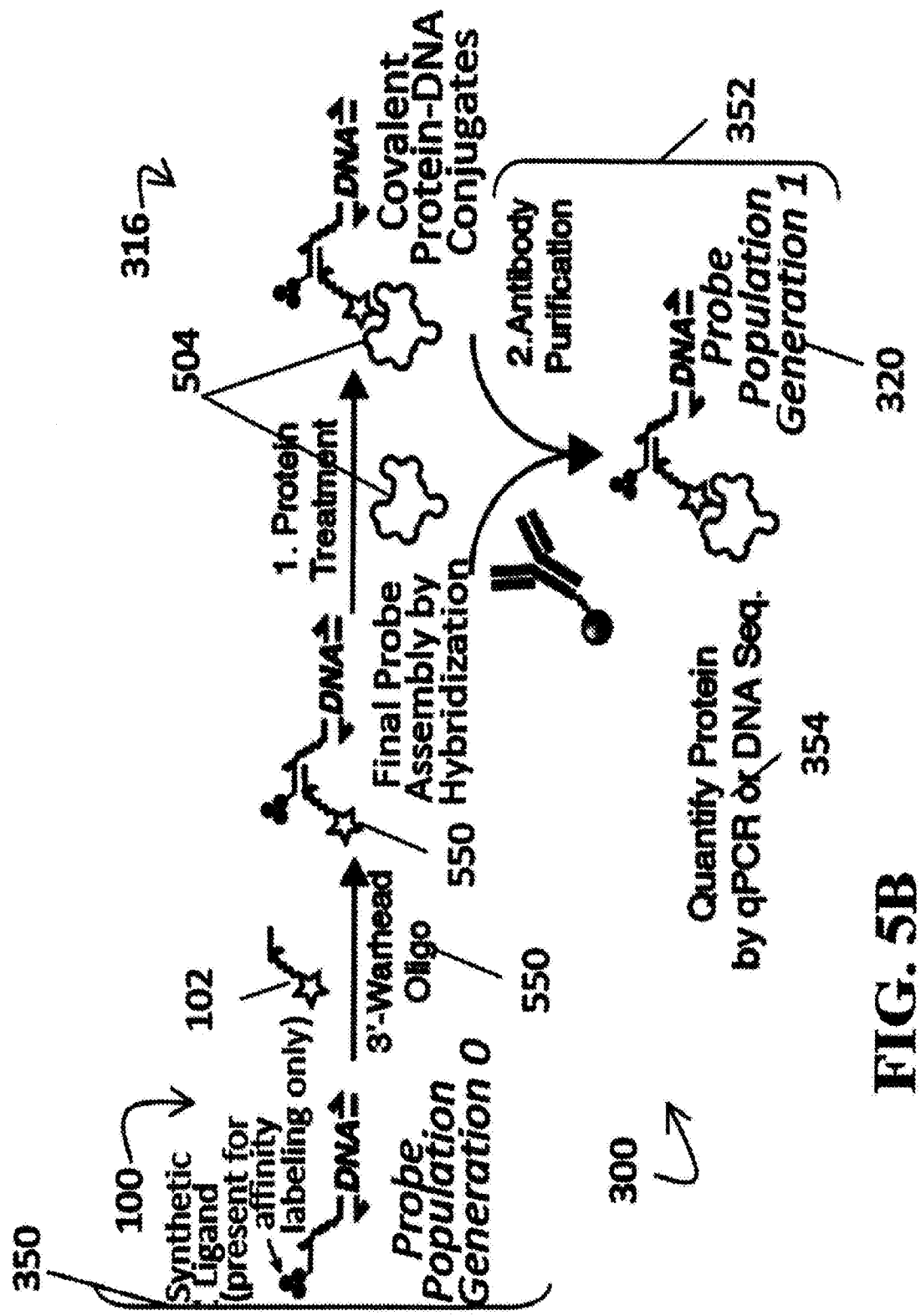

Referring now to FIGS. 5A and 5B, exemplary embodiments of the DNA-encoded probes 100 of the present disclosure, techniques for synthesizing the same, and related experimental results will now be described. In exemplary embodiments, the method 300 for quantifying proteomic activity may be specifically developed for the detection of particular proteomic activities—e.g., farnesyltransferase (FTase), protein kinase and/or protease activities.

Generally, probes 100 for the detection of enzymatic activity can be divided into at least two groups—substrate probes (see FIG. 5A) and covalent probes or protein-directed covalent modifiers, such as mechanism-based reactive groups or general electrophiles paired with synthetic ligands for affinity-based labeling (see FIG. 5B). The substrate and covalent probes may be used interchangeably in many cases; however, one or the other may be more suitable in certain applications depending on the proteins and substrates involved. With covalent probes, the presence of an active protein 504 causes covalent attachment of the protein 504 to the probe 100. There, the attached protein 504 serves as the affinity handle, allowing for the separation of reacted and unreacted probes through antibody purification techniques or the like, such as affinity tags present on the protein. Conversely, with substrate probes modification of the substrate 102 allows for the selective addition of an affinity tag 502 to facilitate the separation of substrates 102 and limit background signal (thereby increasing the overall sensitivity of the assay). The selective pressure 318 can occur via streptavidin, antibody beads, or any other technique known in the art. For both substrate and covalent probes, the amount of DNA in the purified portions can then be determined by quantitative PCR (qPCR) or by high-throughput DNA sequencing and will indicate the amount of enzyme activity in the sample.

Mechanism-Based DNA-Encoded Probes.

Referring to FIG. 5B, probes 100 designed to incorporate mechanism-based covalent modifiers for use with the method 300 are provided. Such mechanism-based chemical probes link to DNA scaffolds 104 for the covalent labeling of active enzymes with DNA, and have been used in the more recently developed activity-based protein profiling (ABPP) approaches.

ABPP is widely used for profiling proteomic samples for enzymatic activity by SDS-PAGE gels or mass spectrometry. Briefly, an ABPP probe contains a protein covalent modifier 550 or 'warhead' (typically an electrophile), a linker or additional specificity element, and a tag for detection (typically a fluorophore or affinity label). In at least one embodiment of the present disclosure, the DNA scaffold 104 is utilized as the reporter and the protein 504 as the affinity tag.

In application, the mechanism-based covalent modifier approach comprises attachment of a ABPP-type probe to an encoding DNA scaffold 104 to achieve the DNA-encoded probe 100. Because many ABPP probes have limited stability in aqueous solutions and can be weakly reactive with DNA, probe assembly in a PCR reaction would likely destroy probe reactivity. To address this issue, in at least one embodiment, the probes 100 are attached to a short oligonucleotide first using a rapid, copper-catalyzed azide-alkyne Huisgen cycloaddition (CuACC), which has been employed in oligo modification. The CuACC reaction is tolerant to a pH range where electrophilic probes show improved stability. After the reaction, the full probe 100 is assembled by hybridization to a longer DNA scaffold 104 with an accepting ssDNA strand, prepared via PCR using a primer containing a polyethylene glycol (PEG) spacer. Alternatively, 55-mer ssDNA encoding strands that can be obtained commercially may be employed.

Incubation of an assembled probe with a protein sample enables covalent modification of the protein 504 with the DNA probe 100 (exposure step 350). Pursuant to method 300, reacted probes 100 are then separated from unreacted probes 100 (purification step 352) using the protein 504 as the affinity tag via immunopurification (IP). The probe 100 assembly-by-hybridization strategy by selective pressure of constructs biotinlyated through oligo hybridization has been validated.

Figure 8A:
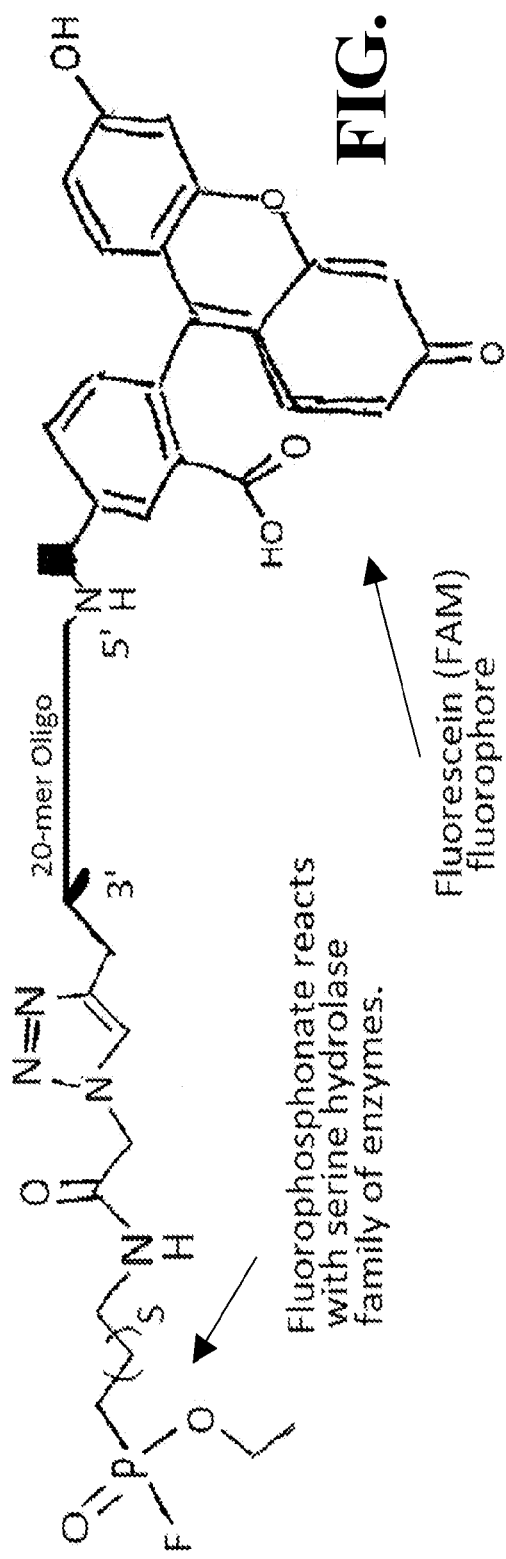
Figure 8B:
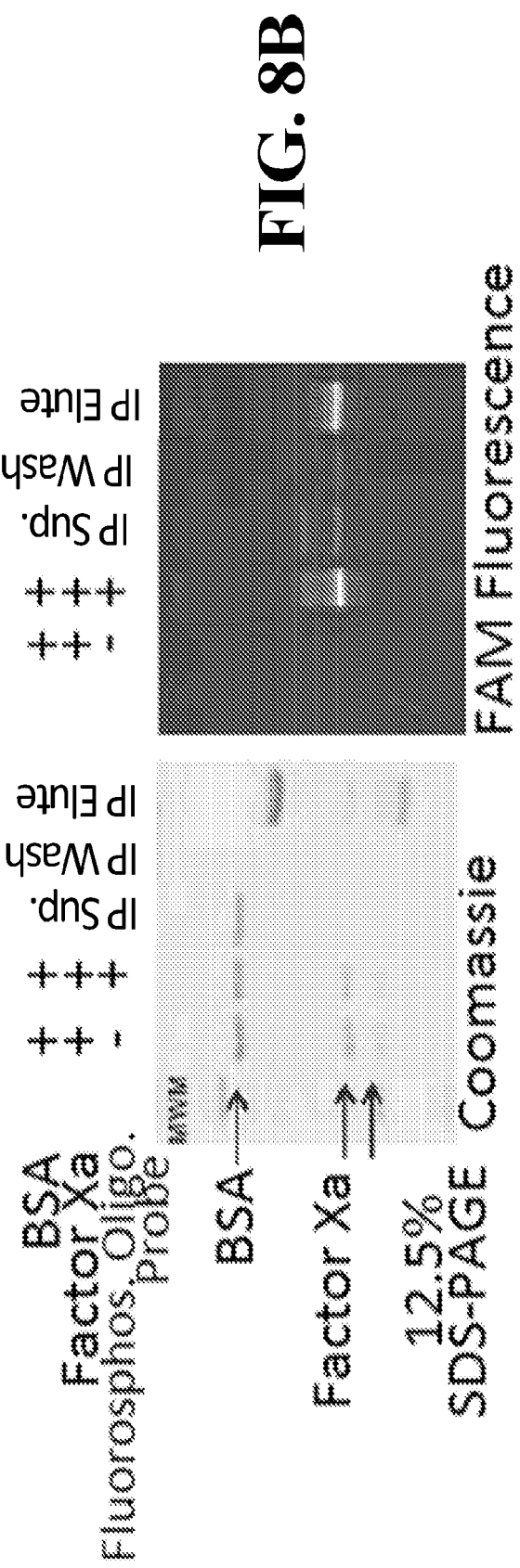

Initial experiments using the methods and techniques provided herein to explore fluorophosphonates (FP) as probes of the serine hydrolase family (which includes several cancer relevant proteases) were conducted. Using a commercially-available, azide-labeled FP, a probe attached to a fluorescein-containing oligo was synthesized (see FIG. 8A). Selective labeling of the serine protease, Factor Xa, was observed (step 350), as was efficient IP of the protein 504 with the attached oligo, which was detected by fluorescence gel imaging (see FIG. 8B). Additionally, the FP oligo-probe 100 was combined with several encoding 55-mer oligos to demonstrate enzyme dependency of signal using the serine protease thrombin (FIG. 8C). This initial test revealed an approximate LOD of 50 nM of the enzyme.

The use of an antibody to the protein of interest 504 in selective pressure 318 introduces an additional specificity element that enables assignment of activity to a particular protein. This is a potential advantage over the substrate probes described herein, which may be less specific in cases of promiscuous substrates 102. While this approach may involve splitting of the sample 312 and, thus, splitting the signal, such losses are offset by the sensitivity of DNA detection.

Levels of sensitivity similar to those observed in iPCR can be achieved using the mechanism-based covalent modifier probes described herein as this system comprises many of the same components. However, notably, instead of the DNA being attached to the antibody (as is the case in iPCR), here the DNA is attached to the protein 504. An alternative approach for activity detection is also to pair the covalently reactive oligos/DNA with a DNA-linked antibody to the target protein. In such cases, detection could be performed via proximity extension or ligation (like PEA or PLA assays, for example), but the readout would provide proteomic activity information.

While the description provided herein related to mechanism-based covalent modifier approach has centered around the protease family, it will be appreciated that this mechanism-based approach may also be used in connection with an acyl phosphate-ATP probe for kinase activity. Such probes react covalently with a conserved kinase lysine in the active site and have exhibited utility in profiling kinase activity by mass spectrometry. ActiveX Biosciences provides an ATP-competitive inhibitor selectivity profiling service using such probes. Unlike the FP probe, the reactivity of a kinase with an acyl ATP reflects only the capability to bind to ATP and not the full activation state of the enzyme, which in certain cases makes labeling efficiency a poor proxy of activity. A more precise activity measurement can be achieved by assessing labeling in the absence and presence of ATP-competitive inhibitors, which are dependent on the enzyme activation state.

Substrate Probes and Tagging.

Now referring to substrate probes, one exemplary embodiment of a method 300 for producing the same is as follows. The substrate probe 100 is synthesized on commercially available, 5'-modified 20-mer oligonucleotides. Conjugates may be prepared either by direct peptide synthesis on amine-modified oligonucleotides, by postsynthetic conjugation using copper-catalyzed azide-alkyne cycloaddition, or via any other process now known or hereinafter developed. Such oligonucleotides may then be used as primers in a PCR to append substrates 102 to specific encoding constructs 104 (140-mer DNAs). As previously noted, encoding constructs 104 comprise one or more barcode regions 108, which may be unique and thus used as an identifier. In at least one exemplary embodiment, the encoding constructs 104 contain two unique 20-mer barcode 108 regions directly within common end-priming regions, which may be used for specific amplification in qPCR.

As is known in the art, any of the proteins or probes 100 (covalent or substrate) may incorporate the use of tagging techniques to assist with purification. Furthermore, any type of suitable tags may be employed including, biotin, genetically-modified labels, or any other affinity label. Additionally or alternatively, immunopurification techniques may also be employed. Biotinlyation of the substrate probes, in particular, can result in a significant amount of labeling of the DNA scaffold 104 with biotin (for example, where method 300 is utilized as a protein kinase A assay). Under certain circumstances, this has been found to govern the level of background signal around about 0.1% relative to complete phosphorylation, which typically limits the lower limit of detection (LOD) and also sets the effective dynamic range of the assay at about 2-logs (without resorting to sample dilutions). Indeed, the purification of biotinylated DNA from untreated, non-biotinylated constructs 104 routinely results in an undetectable amount of background. Because the background signal sets the sensitivity as a function of fractional turnover (about 0.5%), using a peptide substrate 102 with a higher $k_{cat}/K_m$ provides increased sensitivity.

Figure 7A:
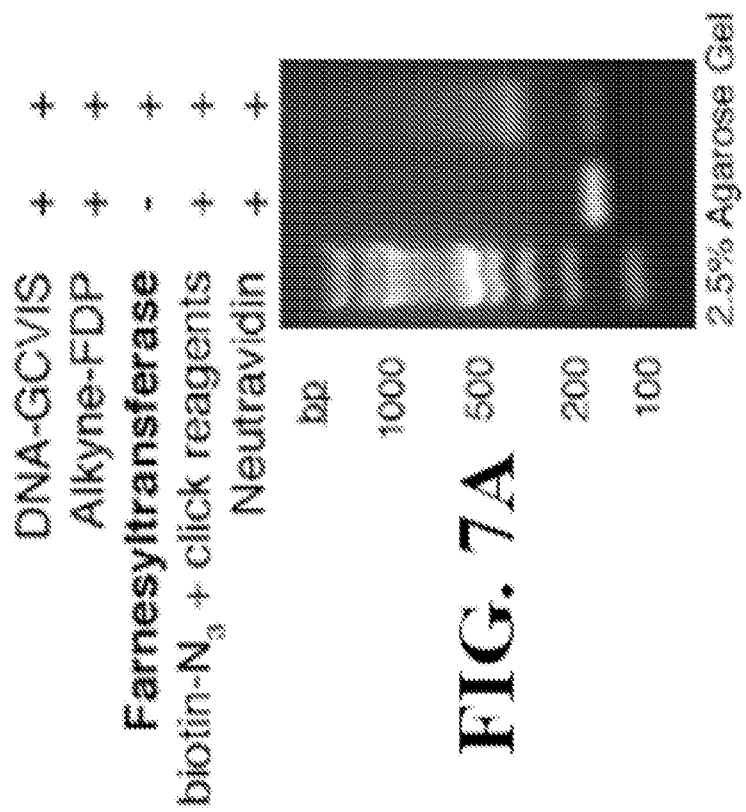
FIGS. 7A-7D show results associated with enzyme-dependent biotinylation and purification of peptide-DNA conjugates according to the present disclosure, with FIGS. 7A-7C indicative of gel shift analysis results of enzyme product-selective labeling, with approx. 140-mer FTase substrate in FIG. 7A, 140-mer PKA in FIG. 7B, and 500 ng portions of 180-mer Caspase 3 in FIG. 7C, all of which associated with peptide-DNA conjugates treated using modification procedures described in the present disclosure. Prior to gel analysis, purified DNAs incubated with 4 μg neutravidin (deglycosylated avidin, ThermoFisher) as indicated.
Figure 6E:
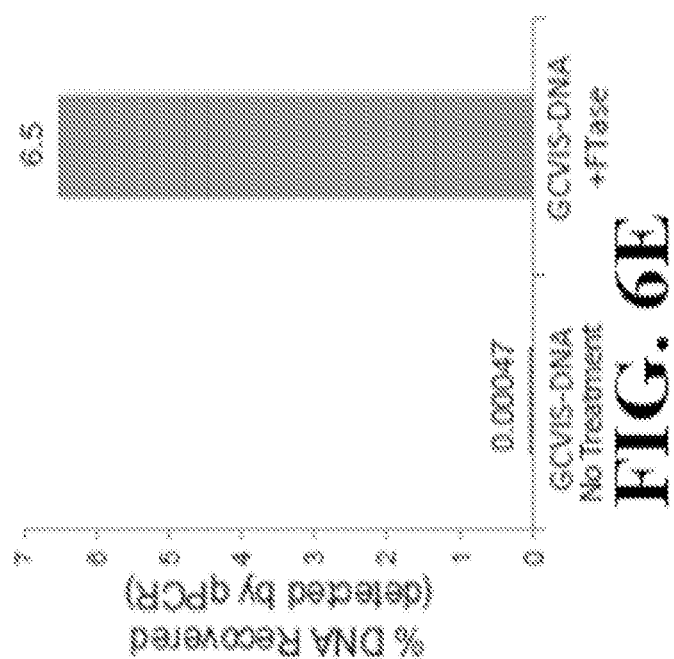
Figure 7B:
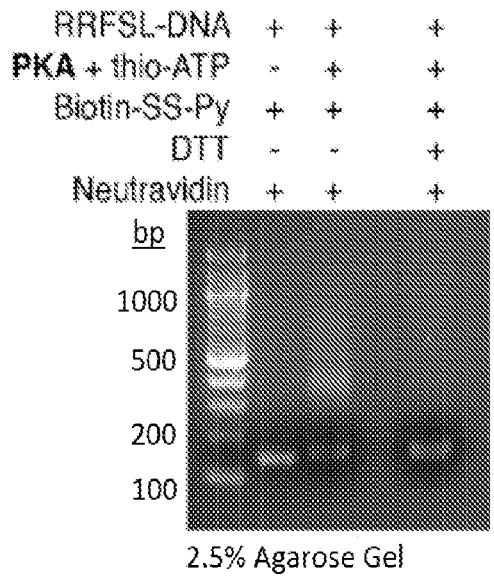
Figure 7D:
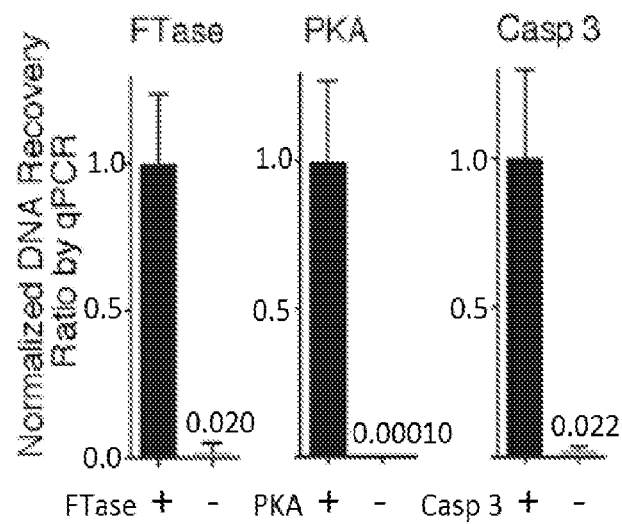
Figure 7C:
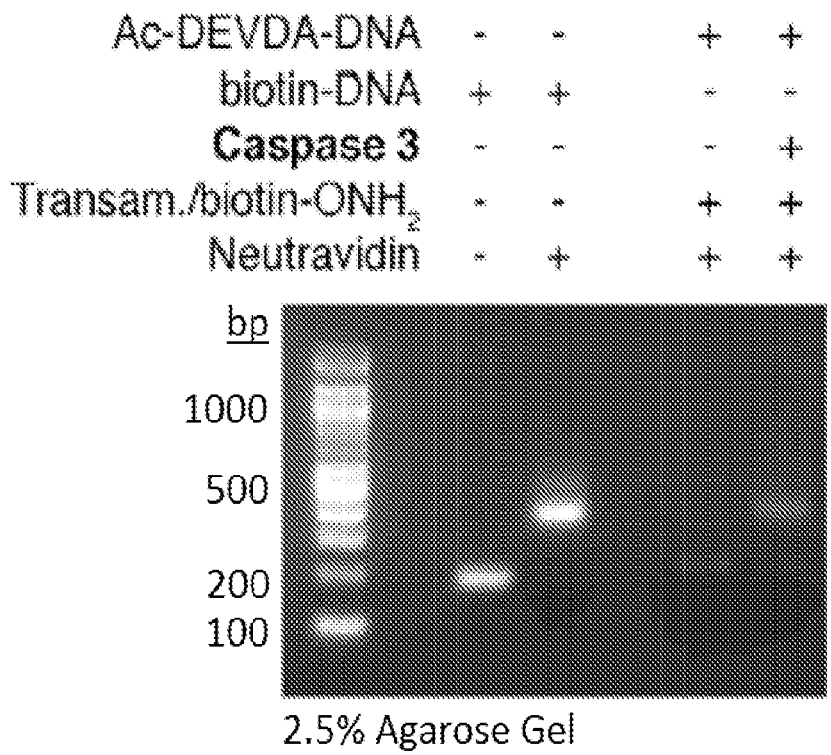
Figure 10A:
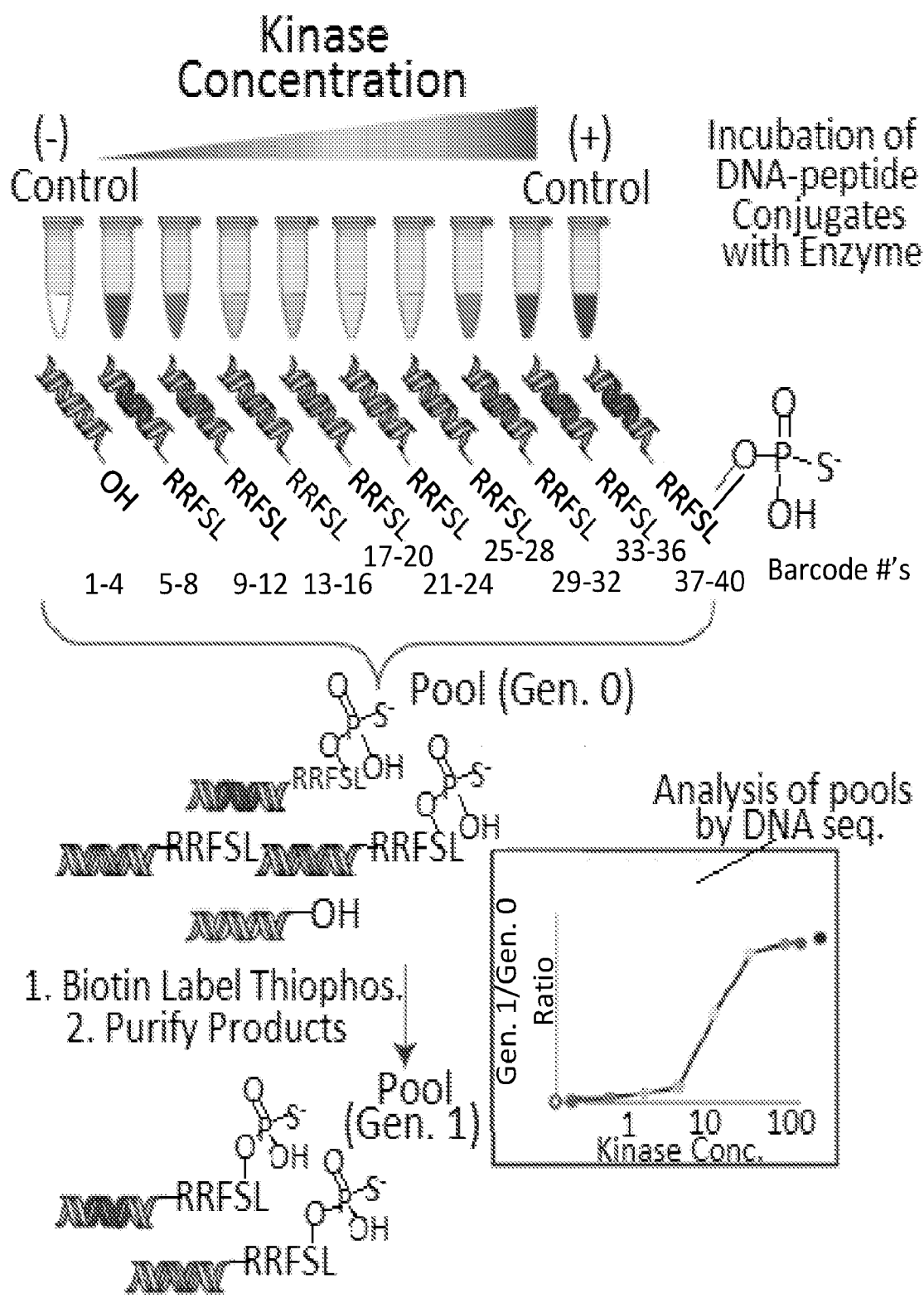
FIGS. 10A-10C show: a schematic view of a method according to the present disclosure modified for the multiplexed detection of enzymatic activity using DNA-encoded probes (FIG. 10A); and plots of relative DNA read ratio vs. FTase and PKA concentrations (FIGS. 10B and 10C, respectively) resulting from the method of FIG. 10A, with the insets in FIGS. 10B and 10C showing the low turnover range on a linear scale.
Figure 10B:
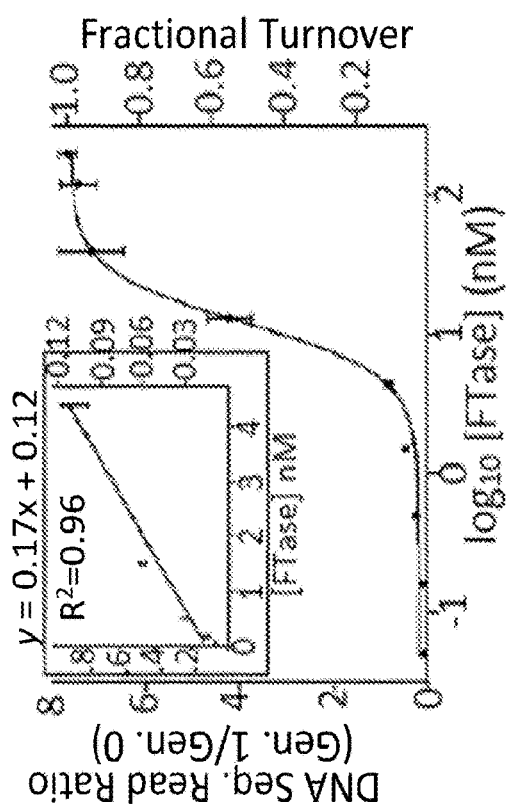

FIGS. 6A-6C illustrate the chemical formulas for selectively labeling enzyme products 314 using a chemical biotinylation approach for FTase (FIG. 6A), protein kinase (FIG. 6B), and caspase 3 enzyme products (FIG. 6C). Further, FIG. 10B shows an agarose gel displaying results indicative of biotinylation of kinase products as detected by gel shift. Specific examples of the preparation of biotinylated probes are provided herein. The product-selective labeling schemes described were validated on peptide-DNA conjugates by gel shift assays through binding to avidin (FIGS. 7A-7C) and by enrichment with streptavidin beads and qPCR analysis (FIG. 7D).

Transferase Assays.

FTase, protein, and caspase 3 were selected for study in connection with the method 300 because they all have potential for generality in detecting activity of a number of biologically important enzymes. In addition to FTase, many transferases accept alkyne modified substrates containing click labels (azides (azido-biotin) or alkynes, for example) to enable purification. FIG. 6A shows an example of such a chemical biotinylation approach for FTase, with FIGS. 6E and 6F verifying the methods success (FIG. 6E indicative of the selective biotinylation of FTase as detected by the gel shift and FIG. 6F showing a bar graph indicating the successful streptavidin purification and qPCR detection thereof). This assay approach of method 300 can be easily extended to other enzymes, such as glycosyltransferases (several azido sugars are commercially available), methyltransferases, acetyl transferases, and palmitoyltransferases.

Protein Kinase Assays.

Similarly, numerous protein kinases have demonstrated the ability to accept thio-ATP as a substrate, with subsequent labeling with biotin pyridyl disulfide (biotin-SS-Py). For example, and without limitation, gamma-thio ATP may be used with kinase substrate probes 100 as a co-substrate with serine/threonine kinases to allow for the selective tagging of products 314 with a biotin affinity tag 402 via disulfide bond formation. Subsequent purification with streptavidin magnetic beads separates products 314 from substrates 102 and allows for the quantification activity by quantitative DNA detection (see FIG. 6B).

Notwithstanding the foregoing, the use of thio-ATP does have some drawbacks under certain circumstances. For example, thio-ATP may not be useful in cell lysates due to the presence of endogenous ATP. Kinases typically show a significant preference for the natural substrate, thus the presence of ATP can lower assay sensitivity. Removal of ATP from the sample 312 is complicated and burdensome and, as such, not a viable option. However, the presence of endogenous thiols in lysates is not a complicating issue with respect to the method 300 because DNA probes can be selectively isolated after kinase treatment using a nucleic acid purification prior to treatment with activated disulfide biotin. In at least one embodiment, Qiagen silica column kits, solid phase reversible immobilization beads (SPRI beads, Agencourt), and phenol/chloroform followed by ethanol precipitation may be used for this purpose.

In at least one embodiment, phosphate affinity reagents may be used in connection with method 300 for the purification of kinase products. A form of immobilized metal affinity chromatography (IMAC, commercially available as Phos-tag) may be particularly useful as there is a clear separation of DNA constructs bearing a single phosphomonoester from control constructs on Phos-tag containing acrylamide gels. An alternative approach, which is applicable only for tyrosine kinases (e.g., spleen tyrosine kinase (Syk) and Lyn), uses the natural ATP cosubstrate and relies on the use of a broad specificity anti-phosphotyrosine antibody for selective purification of enzyme products (see FIG. 6C).

Figure 11A:
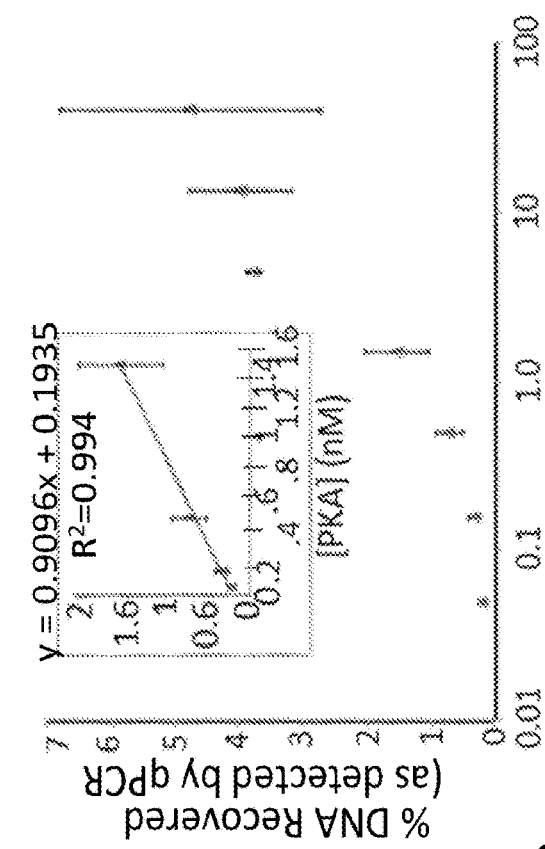
FIGS. 11A and 11B show plots representative of multiplexed detection of: 1) PKA activity (FIG. 11A), with kinase dependent recovery of DNA as detected by qPCR; 32 DNA constructs with the PKA peptide substrate were incubated at 8 different PKA concentrations; samples were pooled, biotinylated, and streptavidin purified; constructs were quantified in the purified pool with specific primers in qPCR; and 2) Lyn activity (FIG. 11B); kinase dependent recovery of DNA as detected by qPCR; 15 DNA constructs with the Lyn peptide substrate were incubated at 5 different Lyn concentrations; samples were pooled and immunopurified.
Figure 11B:
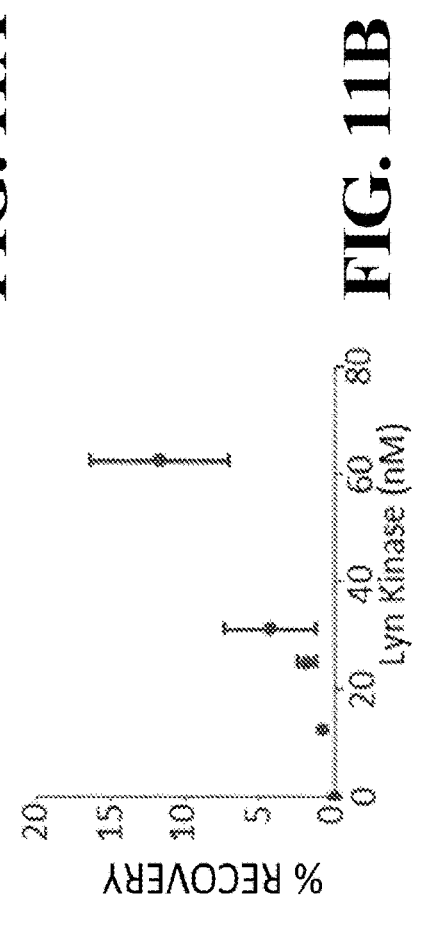

The inventive method 300 hereof has been tested in connection with (although is not limited to) the detection of both protein kinase A (PKA) and Lyn kinase activity. In such tests, peptide substrates 102 (RRFSL for PKA and AIYAA for Lyn) were synthesized from commercially available 5'-amine-modified oligonucleotide, with the peptide subsequently added using established procedures for Fmoc-amino acid chemistry on DNA and/or by PCR. In a 32-way multiplexed assay for PKA (32 unique DNA constructs 104 with 4 of each exposed to 8 PKA concentrations; samples were pooled, biotinylated, and streptavidin purified; constructs were quantified in the purified pool with specific primers in qPCR), the enzyme dependency of the DNA signal was demonstrated as detected by qPCR and a lower limit of detection (LOD) was determined—around 50 pM PKA (see FIG. 11A). FIG. 11B evidences biotinylation of kinase products as detected by gel shift. About 100 attomoles of PKA and 10 femtomoles of the peptide substrate DNA probe 100 were required to reach the LOD.

Now referring to FIG. 11C, the results of multiplexed detection of Lyn tyrosine kinase activity similarly indicated that the LOD for this assay was, at most, 100 Pm (see FIG. 6D for a schematic of the selective affinity tagging and purification steps). Furthermore, the background signal for this assay was below the qPCR LOD due to the high specificity of the anti-phosphtyrosine antibody and the mild elution using phenyl phosphate.

Protease Assays.

Still further, an N-terminal labeling approach could be applied to the cleaved products of any endoprotease. For example, protease products are selectively biotinylated by introduction of a N-terminal ketone by a transamination reaction. Labeling with biotin aminooxybiotin forms a stable oxime linkage thereby enabling purification. Subsequent purification (step 352) with streptavidin magnetic beads separated products 314 from substrates 102 and allowed for quantification of activity by DNA detection (step 354). To validate this approach, an optimal peptide substrate 102 (DEVDA) for caspase 3 was synthesized on a DNA scaffold 104. An exemplary scheme for selective affinity tagging of protease products pursuant to this method is shown in FIG. 6C. Incubation of the peptide-DNA probe 100 with an excess of enzyme and subsequent labeling (step 350) and purification (step 352) resulted in about a $10^5$ difference in DNA recovery versus non-enzyme treated (see FIGS. 9A-9C).

Probe Stability.

A potential pitfall for the method 300 and probes 100 of the present disclosure is the possibility of nuclease degradation of probes in complex biological samples. Accordingly, to investigate the utility of DNA-encoded probes in complex mixtures, method 300 was performed using caspase 3 in lysates from HeLa cells with and without staurosporine treatment to induce apoptosis. The results were then compared against those obtained using a colorimetric substrate probe (Ac-DEVD-pNA, pNA=para-nitroaniline) as shown in FIGS. 9D and 9E.

qPCR tests with 140-mer constructs showed no appreciable degradation over 30 minutes in HeLa cytoplasmic lysates (data not shown). Similarly, as evidenced in FIGS. 9D and 9E, degradation did not interfere with caspase 3 activity detection in cell lysates. The approximate 6-fold increase in caspase activity observed by qPCR (see FIG. 9D) was consistent with the colorimetric assay and with previous reports. Accordingly, method 300 successfully detected caspase activity in a complex sample at least as well as conventional commercial assays. Additionally, the DNA of the probes 100 were not negatively affected by the nucleases in the cell lysate. While some degradation of the DNA would not preclude detection, minimal DNA degradation of the probes was observed in the cell lysate over a 90-minute incubation period. As expression of several nucleases are induced in apoptosis, this is a stringent test for probe stability and thus indicates that the probe of the present disclosure exhibits significantly stability. Notwithstanding the foregoing, in the event degradation becomes a concern, it is within the scope of method 300 to add broad-spectrum nuclease inhibitors to the sample 312, to add an excess of DNA to overwhelm nucleases, and/or to incorporate nuclease resistant phosphothiolate linkages 106 in the DNA construct 104.

Multiplex Assays.

Figure 10C:
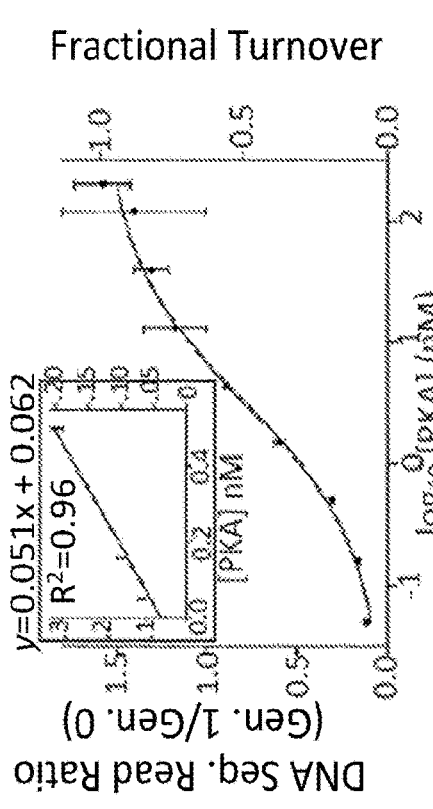

Multiplexed variations of the method 300 were also performed using sets of peptide-DNA constructs with unique DNA sequences and several enzyme concentrations of FTase, protein kinase, and protease. Here, and particularly if using qPCR for step 354, the barcodes 108 of the probes 100 may be orthogonal so that they can also be used as primers to specifically detect a desired construct through DNA amplification. FIG. 10A shows a schematics representative of the steps of method 300 in connection with the multiplexed detection of enzyme activity by DNA-encoding. Through parallel DNA sequencing and/or qPCR, probe frequency changes were detected among a pool of approximately 40 sequences in response to enzyme exposure, biotin labeling, and affinity purification. For each of the three enzymes, dependency of the assay signal on enzyme concentration was observed (only FTase and PKA results shown in FIGS. 10B and 10C). Perhaps more specifically, FIGS. 10B and 10C illustrate plots of relative DNA read ratio versus FTase and PKA concentrations, respectively. Results were similar to quantifying DNA by read ratio with parallel high-throughput DNA sequencing (Illumina) or by qPCR using construct-specific primers, although variance in signal was generally greater using qPCR. The insets in FIGS. 10B and 10C show the low turnover range (<20%) of the FTase and kinase assays on a linear scale.

Enzyme Inhibition.

In at least one embodiment, the method 300 may also be utilized as a method for detection of enzyme inhibition (as opposed to activity, which has been discussed thus far). To demonstrate the utility of the method 300 for detection of enzyme inhibition, the half maximal inhibitory concentrations ($IC_{50}$) were measured for the FTase inhibitor tipifarnib (see FIG. 12A) and the protein kinase a (PKA) inhibitor staurosporine (see FIG. 12B). Furthermore, to test the feasibility of inhibition assays for HTS, the separation of sets of partially biotinylated (at or about 10%) and non-biotinylated DNA constructs 104 by parallel DNA sequencing was assessed (see FIG. 12C). This test was designed to mimic HTS conducted at 10% enzymatic turnover. The results showed little contribution of the construct sequences to the observed signal. As a mock assay, the results yielded a Z' factor of 0.5, which is indicative of robustness. Random sampling of sequencing reads indicated that the read number per sample could be reduced to approximately 600 without affecting the Z' factor.

The use of DNA as a signal has advantages of high sensitivity through DNA amplification. In these three assays, the limits of detection (LOD) observed were generally around 2% of the full substrate turnover (FIGS. 7D, 10B, and 10C). This background signal was consistent with the level observed in the separation of biotinylated and nonbiotinylated DNA constructs (see FIG. 11C). Improvements could be achieved through optimized streptavidin purifications or by use of alternative affinity tags. Nonetheless, the method 300 of the present disclosure (and the various embodiments thereof described herein) require a very small amount of sample for detection which, in theory, is limited only by adequate sampling of the DNA probes 100. In the kinase assay for example, detection of activity by qPCR at the LOD (about 50 pM) would require less than 1 nL of sample. In addition, this sensitivity allows assays to be conducted at low concentrations (about 10 nM or lower) of substrate peptide-DNA probes. With these concentrations being well below enzyme Michaelis constant Km values, these assays are highly sensitive to inhibition.

In addition to facilitating analysis of many samples, the collective manipulation and selection of a pool of DNA-encoded probes from several samples is important for precise and quantitative activity detection. Pooled probe manipulation allows any inefficiencies or variability in chemical modification, DNA purification/precipitation, or affinity purification steps to be normalized across the pool. This normalization enables precise assays; indeed, in general, low percent coefficients of variation (% CV) were observed. For example, in the determination of the $IC_{50}$ value for tipifarnib by DNA sequencing (FIG. 11C), the overall average % CV was at or around 10%. Additionally, the recovery of a particular probe relative to a positive control within the pool allows determination of fractional turnover and a quantitative measurement of enzyme activity.

In the protease assay, a DNA construct with the fully cleaved peptide product was doped into the pool. In the FTase and PKA assays, probes treated with an excess of enzyme were used as positive controls. In at least one embodiment, negative controls that are established in the assay background may also be employed—either as DNAs lacking peptide substrates or peptide—DNA conjugates that were not treated with enzyme. The advent of DNA-encoded small-molecule libraries has enabled the application of selection-based approaches to large collections of synthetic molecules. Assays with DNA-encoded probes will enable many of the same benefits realized in those approaches to be applied to any molecule of interest that is free in solution, such as molecules within existing library screening collections. As probe manipulations (covalent modifications and DNA purifications) and affinity selections are conducted on a probe pool, costs and effort increase only marginally as more assays are combined. The high sensitivity achieved by DNA amplification allows assays to be massively miniaturized, conserving costly enzyme and compound stocks. The high capacity of parallel DNA sequencing would readily allow concurrent assessment of approximately 150,000 samples (at present levels, for example, allotting 1,000 reads per sample).

DNA-encoded probes could also be useful in activity profiling of proteomic samples. DNA-assisted protein detection approaches, such as immuno-PCR and proximity extension assays, have demonstrated remarkable sensitivity and multiplexed analyte detection. Peptide substrates are commonly employed to detect protease and protein kinase activities in fluorescence, mass spectrometry, and microarray approaches. Using sets of validated peptide substrates and identifying DNA barcodes, the inventive DNA-encoded probes 100 hereof can be used to concurrently assess multiple activities in a manner analogous to a peptide microarray.

In sum, the novel methods of the present disclosure allow for sensing sample characteristics through exposure, selection, and DNA sequence analysis of DNA-encoded probes. Furthermore, the approaches hereof allow for the accurate detection of enzymatic activities. Development of suitably responsive probe molecules as described herein will allow this general approach to be extended to the detection of other stimuli by DNA analysis.

Clinical Applications.

The catalytic subunit of PKA, for example, is significantly elevated (5-10 fold) in the bloodstream of cancer patients. This extracellular PKA (ecPKA) and other ectokinase activities have recently garnered interest as useful cancer markers. However, the low levels of activity present challenges for detection using conventional methods. Conventional techniques to detect ecPKA in patient samples have relied exclusively on radioactive assays; however, exposure to radioactivity is problematic for those performing the assays, as is the cumbersome amount of paperwork and red tape associated obtaining approval for the use of radioactive assays and the disposal of radioactive waste. However, the PKA level in the serum of healthy individuals has been estimated at about 3 pM, which is below other conventional assay detection limits and, thus, problematic. Using the techniques described herein, a DNA-peptide substrate probe was synthesized based on the highly specific protein inhibitor for PKA—protein kinase inhibitor (PKI)—with the sequence GRTGRRNSI. This peptide has about a 100-fold greater $k_{cat}/K_m$ than the RRFSL peptide for PKA and provided a significant increase (e.g., a 100-fold) in assay sensitivity. Accordingly, the method 300 for detecting proteomic activity using DNA-encoded probes could provide sensitivity for detection of PKA activity in the bloodstream of a subject to accurately identify upregulation, for example, of ecPKA, which can be indicative of cancer.

Similar to the upregulation of PKA, the dysregulation of nonreceptor tyrosine kinases (NRTKs) is frequently observed in cancer. Syk and Lyn are tyrosine kinases in the 32-member class of NRTKs. In at least one exemplary embodiment, the method 300 may be used in conjunction with selective peptides that are highly selective for the NRTK family. For example, using a peptide substrate sequence for Syk, an oligo-peptide conjugate can be synthesized pursuant to the present disclosure and assay conditions optimized using purified Syk. Thereafter, Syk activity in cell lysates can be detected and quantified according to method 300. Likewise, a DNA-encoded probe assay can also be developed for Lyn using an optimally selective peptide for Lyn kinase. Using the purified enzymes, the multiplexed detection of both Syk and Lyn activity can be achieved in control enzymes mixtures using method 300 and the level of crosstalk of the assays may be determined.

As previously stated, the systems and methods hereof rely upon the use of specific DNA-encoded probes 100. These probes 100 extend the ease of use, sensitivity, and multiplexing benefits observed in DNA-assisted immunoassays and aptamer assays to the detection of enzyme activity and other functional proteomic information when used in connection with the selection-based sensing techniques of the present disclosure. Indeed, the ability of DNA to be amplified allows for highly sensitive detection. As previously described, for many important applications—such as the early detection of cancer-causing biomarkers—the sensitivity of an assay can be limiting. The information encoding abilities of DNA allow for extensive multiplexing of sample analysis, which is a major advantage of the systems and methods of the present disclosure over current, conventionally-available methods for proteomic profiling such as ELISA and mass spectrometry. The systems and methods hereof do not require additional specialized equipment or fabrication of unique devices, and the costs associated with DNA sequence analysis are dropping rapidly. Sequencers are becoming increasingly ubiquitous and are moving into the clinic for a number of diagnostic applications. Furthermore, the novel activity probes 100 hereof may be designed to be indicative of several proteomic functions including, for example and without limitation, enzymatic activity, affinity, and reactivity.

Ligand Binding Affinity.

In addition to detecting enzymatic activity, the systems and methods of the present disclosure (and the concepts underlying the same) may be alternatively leveraged to detect ligand (or synthetic small molecule) binding affinity. DNA-encoded combinatorial libraries have become useful sources of drug lead and molecular probe compounds. However, achieving sufficient enrichment of ligands from DNA-encoded libraries for detection has historically been difficult, particularly for low affinity ligands within highly complex libraries. A critical step in these campaigns is the in vitro selection, where binders (those ligands that have a high affinity for binding with respect to a particular molecule) are distinguished from non-binders.

Generally, the enrichment of ligands from DNA-encoded libraries generally involves immobilization of a purified target protein onto a physical matrix (e.g., biotinylated protein on streptavidin magnetic beads, His-tagged protein on Ni-NTA resin, or chemical modification of resin/beads with protein), incubation of the target within the library, washing of the support, and finally elution of the bound ligands. While solid-phase selections have been successful in a number of applications, in certain cases, such selections fail to yield enrichments significant enough to indicate potential ligands even when using next-generation DNA sequencing. This approach has several limitations: background binding to the support matrix, potential for multivalent binding, limited control over protein concentration, and loss of native properties of the target protein upon immobilization. In addition, the required washing steps make solid-phase selections particularly challenging for enrichment of low affinity ligands. To address these limitations, a number of approaches have been developed including isolation in kinetic capillary electrophoresis, interaction dependent PCR/primer extension, exonuclease protection through DNA-programmed affinity crosslinking, and co-compartmentalization with DNA-linked protein targets in emulsion droplets.

In at least one embodiment of the present disclosure, a novel method 1300 for detecting ligand binding activity of proteins is provided. In general, the method 1300 comprises a variation of method 300 applied to ligand (or synthetic small molecule) binding. Notably, in addition to the steps of method 300, method 1300 further comprises a crosslinking step 1351, where DNA-linked ligands 1310 are crosslinked to target/binding proteins 1312 and subsequently attached to a reactive group 1314 post-synthetically via DNA hybridization. This crosslinking effectively traps the resulting ligand-protein complexes 1316 while in solution such that the ligand-protein complex 136 can maintain its integrity during subsequent selection and/or purification steps. Similarly, crosslinking allows sample pooling for assessment of ligand binding from many samples collectively, as with method 300 (FIG. 3B). In this manner, the method 1300 makes it possible to assess ligand binding affinity. This has many benefits in application, for example, multiple DNA-linked ligands can be assessed for binding quantitatively through titration of protein target concentrations in several samples. Also, this method could be applied in ligand displacement assays, as is commonly employed with fluorescence polarization assays with fluorophore-labeled ligands or other assay formats, for small molecule screening (as outlined in method 400) for ligands that displace the DNA-linked ligand, thereby diminishing crosslinking efficiency.

Importantly, method 1300 includes several steps akin to those of method 300—for example, similar to the probe 100 creation and exposure portions of step 350/method 300, method 1300 involves the tethering of a ssDNA oligonucleotide to a DNA-encoded molecule to enable attachment of a reactive group 1314 post-synthetically via DNA hybridization (step 1350). Likewise, the cross-linked ligand/reactive group complexes are also subsequently purified or eluted from the resulting pool (purification step 1352, similar to purification step 352). As previously noted, crosslinking the ligand/protein (i.e. probe) is an added step (step 1351) in method 1300 because it effectively traps ligand-protein complexes while in solution and allows for stringent washing conditions to be applied in the subsequent purification (step 1352) and also allows for sample pooling to enable collective sample assessment after quenching of the reactive group.

Figure 13:
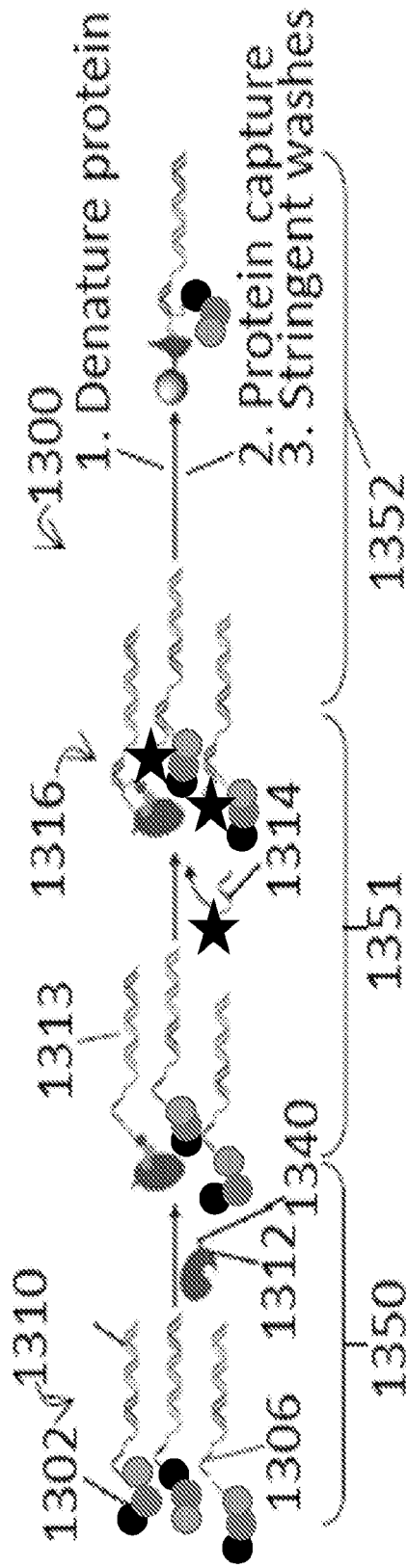
FIG. 13 shows a schematic flow chart depicting an exemplary method for enriching DNA-linked ligands by crosslinking to a target protein pursuant to the present disclosure.

Now referring to FIG. 13, in at least one embodiment, at step 1350 a small molecule ligand 1302 (or several DNA-encoded molecules within a library) is/are appended via a ssDNA tether 1306 to the 5' end of a dsDNA construct 1304 to produce a DNA-encoded small molecule 1310. Thereafter, the small molecule 1310 is exposed to a target protein 1312 and, if the ligand 1302 has an affinity for binding, the DNA-encoded small molecule 1310 binds the same (also step 1350). After equilibration with a protein target 1312, at step 1351 a reactive group 1316 containing ssDNA that is complementary to the to the tethered ssDNA 1306 is added to allow for crosslinking of the DNA-linked small molecule 1302 to the protein target 1312. All library members (i.e. ligands 1302) contain the same 20-mer ssDNA sequence 1306 tethered to the unique dsDNA (ligand encoding) construct 1304. This allows a reactive group-ssDNA 1314 to be added by DNA hybridization after library synthesis and for the binding to a protein target 1312, thereby resulting in a dual display of functional moieties on a DNA scaffold 1304 (ligand 1302 and reactive group 1314). Ultimately, the reactive group 1314 may be displayed from the 3' end of the opposite DNA strand 1304 of the resulting crosslinked complex 1313; however, there are a number of variants available with respect to presenting the ligand and reactive groups in dual display fashion. The exact orientation (5' end ligand and 3' end reaction group) could be switched trivially. Similarly, the ligand may be synthesized on a ssDNA without the inclusion of the PEG linker tether.

Following crosslinking step 1351, the target protein 1312 (which comprises an affinity tag 1340) can be denatured without impairing DNA hybridization and captured/immobilized onto a solid support via an affinity tag 1340 (e.g., biotin) or the like. Quenching and washing conditions (which can be stringent) can then be applied to remove non-ligands and maximize the enrichment of the ligands 1302 (step 1352), as well as detection by qPCR or DNA sequencing (step 1354 (not shown in FIG. 13), similar to step 354 of method 300). Similarly, proteins could be captured without denaturing using common affinity tags (e.g. biotin, His-tag, GST-tag) or using antibodies (immunopurification) specific to the protein target. In at least one embodiment, qPCR allows for the relative enrichment of known ligands on DNA and DNA sequencing may be employed to identify ligands from DNA-encoded libraries. The ligand affinity may be inferred from rank order of DNA sequence enrichment.

Figure 14A:
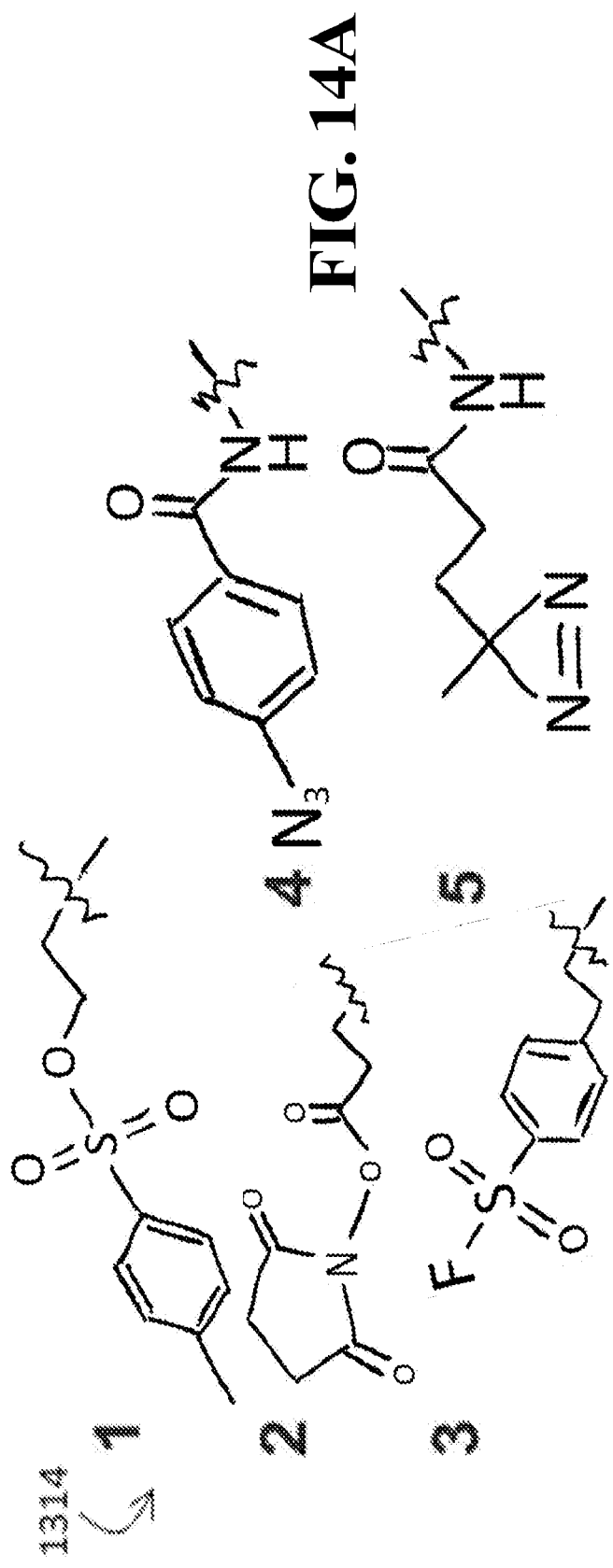
FIG. 14A-14C show: 1) a panel of the chemical structures of potential reactive groups (RG) that may be used in connection with the method of FIG. 13 (FIG. 14A), labeled as follows: 1) tosyl, 2) NHS ester, 3) sulfonyl fluoride, 4) phenyl azide, and 5) diazirine; 2) the chemical structure of a small molecule model ligand Gly-Leu Carboxybenzene Sulfonamide (GL-CBS)-ssDNA 10 nM $K_d$ hybridized to 3'-reactive group-5'-FAM-ssDNA' pursuant to embodiments of the method of FIG. 13 (FIG. 14B); and 3) a gel showing the results of a SDS-PAGE analysis of reactive group crosslinking efficiencies with GL-CBS ligand to CAII (10 μM CAII, 10 μM BSA, 1.0 μM ligand-ssDNA, 0.75 μM RG-ssDNA') (FIG. 14C)

This approach provides a number of conveniences for the assembly of a DNA-encoded small molecule 1310 with a DNA-linked reactive group 1314. The modularity of the approach allows various reactive groups 1314 to be readily tested with a single ligand construct 1310. Furthermore, reactive groups 1314 with moderate stability can be synthesized on oligonucleotides directly before use and assembled quickly by DNA hybridization. Indeed, a wide variety of reactive groups 1314 may be employed in affinity-based crosslinking approaches. For example, and without limitation, three electrophiles (tosyl (1), N-hydroxysuccinimide (NHS) ester (2), sulfonyl fluoride (3)) or two photoreactive groups (diazirine (4) and phenyl azide (5)) may be synthesized on a 3'-modified, 20-mer oligonucleotide ssDNA (see the reactive group (RG) panel of FIG. 14A) to synthesize reactive group 1314. By way of an explanatory example, in operation, the electrophile of the reactive group 1314 reacts generally with nucleophiles on protein 1312 surfaces to form the crosslink.

Figure 14B:
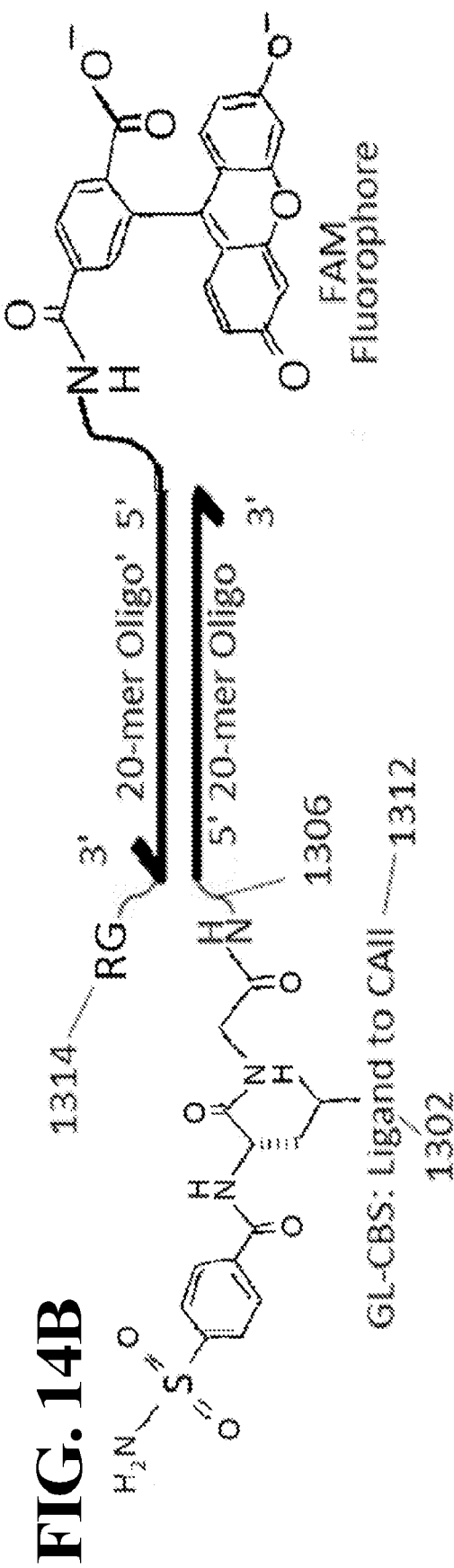

In at least one embodiment, each of the reactive group-containing oligos 1314 also comprises a 5'-fluorescein amide (FAM) modification to facilitate detection of crosslinking. As shown in FIG. 14B, ligands 1302 may be synthesized separately on a 5'-modified, complementary ssDNA. Examples of ligand/receptor pairs may include glycylleucine carboxybenzylsulfonamide (GL-CBS) to bovine carbonic anhydrase II (CAII), staurosporine (STS) to protein kinase A (PKA), and a peptide ligand to the chromodomain of chromobox protein 8 (CBX8).

Crosslinking efficiencies of the reactive group oligos 1314 to target proteins 1312 were assessed when hybridized to ligand-containing oligos 1310. Ligand-ssDNAs 1302/1306 were first incubated with protein 1312 to allow for equilibration prior to the addition of the reactive group ssDNA 1314. After incubation (and, in certain embodiments, irradiation at 354 nm for diazirine and phenyl azide), crude reaction mixtures were analyzed by SDS-PAGE. The crosslinking efficiency of the protein 1312 to DNA for each reactive group 1314 was determined by comparing the FAM fluorescence intensity of the free oligonucleotide to the crosslinked, gel-shifted oligo-protein complex 1316. Crosslinking yields were determined from ratio of the FAM fluorescence of crosslinked CAII (CAII-DNA) to the total crosslinked and non-crosslinked 5'-FAM-ssDNA (DNA). In the ligand directed crosslinking of CAII (see FIG. 14C), efficiencies observed were as high as 36% for phenyl azide (5), and reactive groups NHS ester (2), sulfonyl fluoride (3), and phenyl azide (5) performed similarly. In reactions with the CBX peptide ligand-ssDNA and CBX8 protein, both NHS ester (2) and sulfonyl fluoride (3) gave significant crosslinking (45% and 71%, respectively). With STS-ssDNA and PKA (not shown), NHS ester was the only reactive group 1314 to give substantial crosslinking. Overall for these three ligand-receptor pairs, NHS ester and sulfonyl fluoride reacted much more efficiently than tosyl. Of the photoreactive groups, diazirine consistently gave greater crosslinking yields than phenyl azide.

Figure 14C:
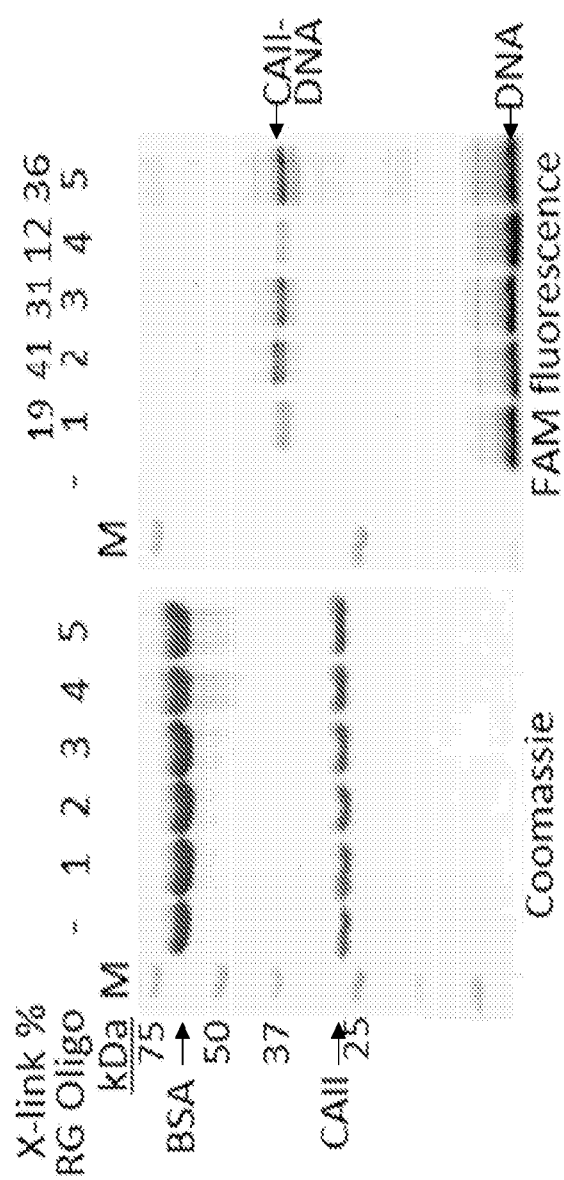

The crosslinking efficiency comparison data indicates that the NHS ester is generally the highest yielding reactive group 1314 for crosslinking and perhaps the exemplary choice when approaching a protein target 1312 de novo. The electrophilic groups were explored primarily due to the highly selective and efficient affinity crosslinking previously demonstrated with tosyl groups in both live cells and animals. Crosslinking with the acyl imidazole group, however, was determined to be reactive with the fluorescein tag in the preparation of a modified oligo and because crosslinking with the electrophiles involves a properly placed, suitable nucleophile on the protein, it was likely the yields would be very case dependent. In exo-mechanism affinity labeling, tosyl groups have shown to react with His, Glu, and Tyr side chains, NHS esters with Lys, and sulfonyl fluorides with Ser, Tyr, and Lys. In contrast, the highly reactive nitrene and carbine species generated by photoactivation of the aryl azide and diazirine, respectively, can insert a number of bonds (C—H or N—H) on the protein. It has been demonstrated that for some protein targets, the acyl imidazole group is more reactive, higher yielding, than the tosyl group. Such demonstrations support investigation into the efficiency of an acyl imidazole reactive group 1314 in crosslinking. Synthesis of acyl imidazole 1314 as shown in FIG. 14B demonstrated reactivity between the acyl imidazole and FAM fluorophore. This observation led to the removal of acyl imidazole from reactive group 1314 and use as shown in FIG. 14C. The description of exo-mechanism affinity labeling illustrates the reactivity of different reactive groups towards specific amino acid residues on proteins—as crosslinking is fundamentally dependent on a properly placed residue on the protein.

Figure 15A:
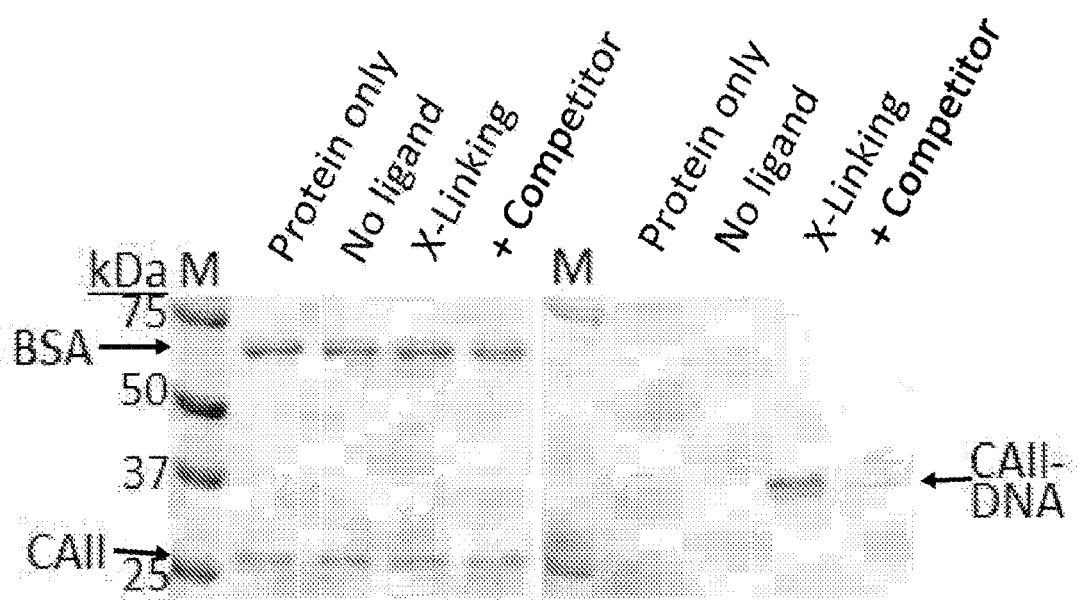
FIGS. 15A-15C show gels indicative of the results of tests on ligand dependency of DNA-protein crosslinking (all DNA constructs were excluded from the protein only lane, no-ligand lanes used 5'-OH-ssDNA in place of ligand-ssDNA), with crosslinking of FIG. 15A CAII with GL-CBS-ssDNA using sulfonyl fluoride (3), FIG. 15B CBX8 with CBX peptide-ssDNA using sulfonyl fluoride (3), and FIG. 15C PKA with STS-ssDNA using NHS ester (2); competitor ligands used were 10 μM methazolamide for CAII, 5 mM SK(me₃)LAF peptide for CBX8, 10 μM STS for PKA.
Figure 15B:
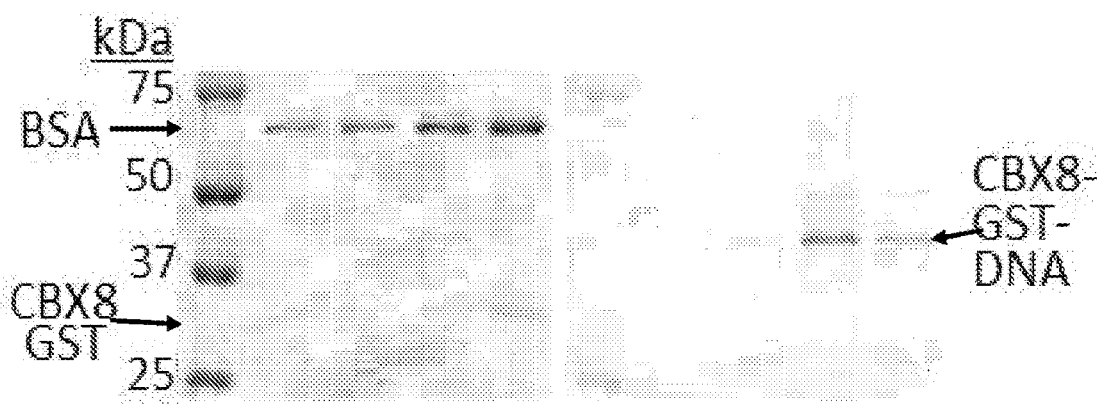
Figure 15C:
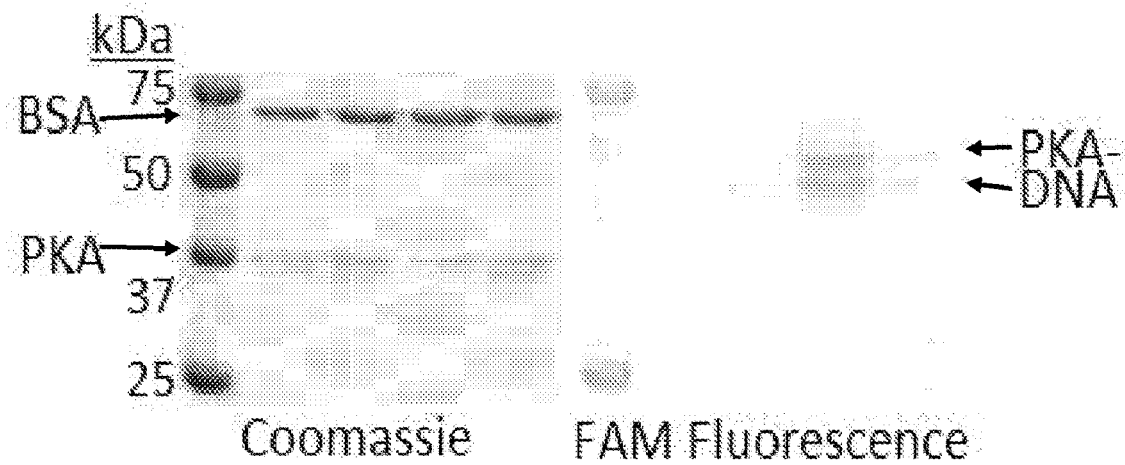

In addition to labeling efficiency, the ligand dependency of crosslinking is important. The non-specific, ligand-independent cross-linking of the target protein 1312 would produce background signal in a binding assay or library selection (i.e. in application). To assess ligand dependency of crosslinking, the three proteins were incubated with the reactive group oligos paired with a non-ligand oligo, ligand oligo, or the ligand oligo in the presence of a competitive ligand (see FIGS. 15A-15C). Little to no crosslinking to the target protein 1312 was observed with the non-ligand oligo, and suppression in crosslinking was observed in all three systems with the addition of a competitive ligand. To assess ligand dependency of crosslinking, bovine serum albumin (BSA) was included in the crosslinking reactions and little, if any, crosslinking to BSA was observed.

Figure 16A:
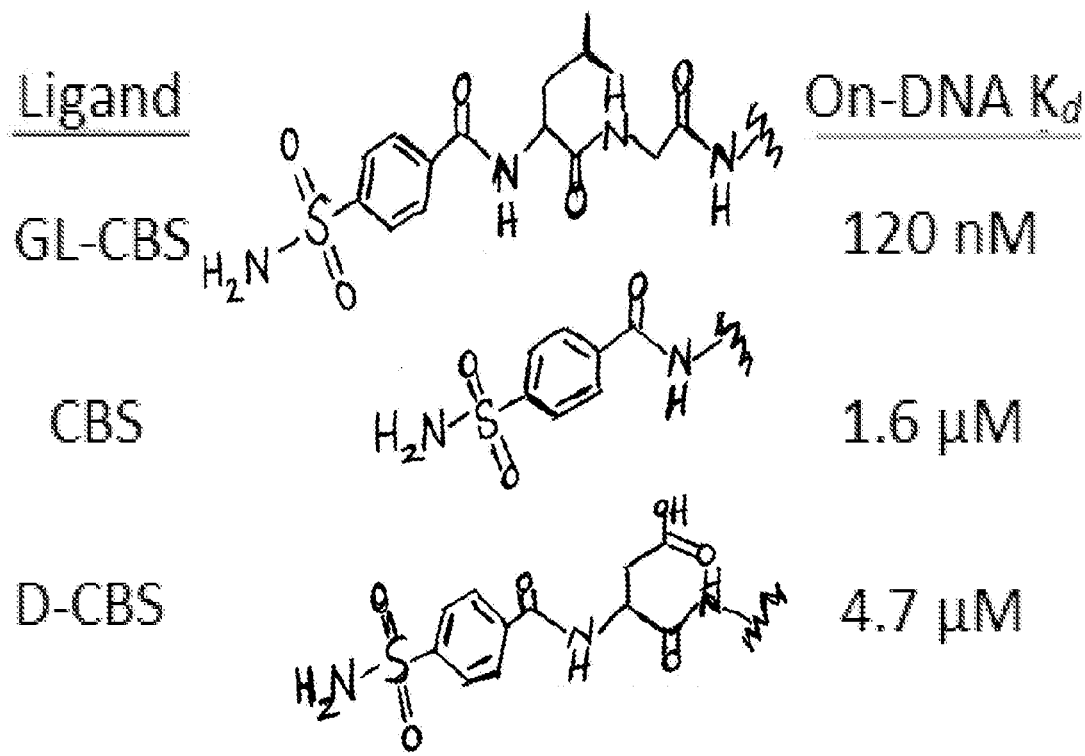
FIGS. 16A-16C show charts and gels associated with affinity-based crosslinking of DNA to CAII with ligands of varying affinity, with FIG. 16A showing three on-DNA ligands with $K_d$'s to CAII as determined by bio-layer interferometry.
Figure 16B:
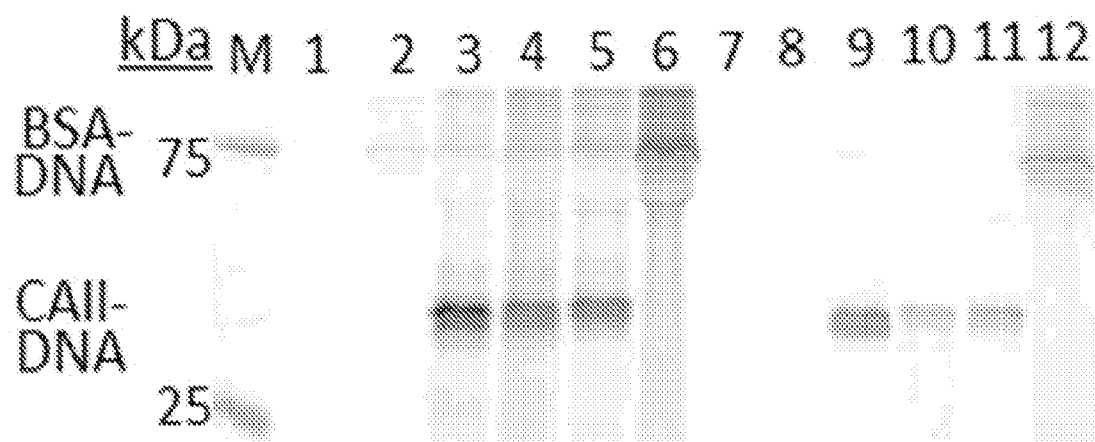
Figure 16C:
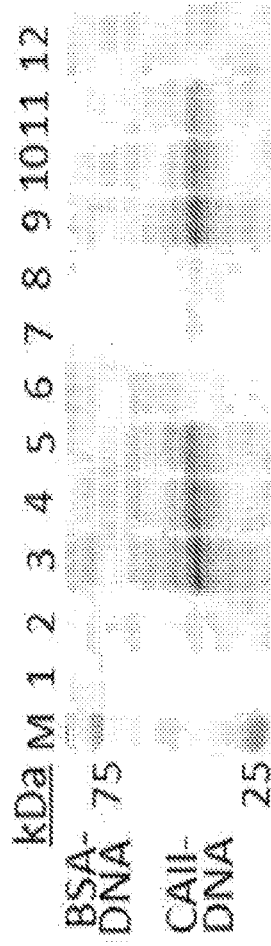

To determine if crosslinking levels were dependent on ligand affinity (particularly for the long-lived electrophile sulfonyl fluoride (3)), three ligands 1302 were prepared on DNA 1304 with varying affinities for CAII (FIG. 16A) and subsequently applied in reactions using either phenyl azide (5) or sulfonyl fluoride (3) (FIGS. 16B and 16C, respectively). The on-DNA affinities were consistent with published reports of the free molecules. Differences in crosslinking was observed at both 10 μM and 1 μM CAII for each ligand 1302 and such differences were consistent with the target protein 1312 concentrations and ligand $K_d$'s with both reactive groups 1314.

In these tests, significant levels of BSA crosslinking were observed when reactive group phenyl azide (5) was paired with the GL-CBS ligand oligo in reactions that lacked the target protein 1312 (FIG. 16B, lanes 6 and 12). This crosslinking likely reflects the propensity of BSA to bind to hydrophobic small molecules and potentially to sulfonamides specifically. Thus, this labeling may still be considered ligand-dependent. Bio-layer inferometry analysis, however, with the GL-CBS ligand and BSA at 10 μM did not indicate binding (not shown).

Encouraged by the results of crosslinking efficiency and ligand-dependency, the crosslinking strategy of method 1300 was applied to enrich ligands 1302 on encoding DNA sequences 1304 in a model selection. However, in application, appending a reactive group 1314 on the 3' end opposite a 5' end DNA-linked small molecule 1310 presented a challenge when considering the construct 1304 architecture and workflow of many DNA-encoded small molecules approaches. PCR or DNA-hybridization is the easiest approach for appending a oligo-linked small molecule to a unique DNA encoding construct. Similarly, small molecule libraries generated by DNA-programmed combinatorial chemistry (DPCC) are constructed on ssDNA, but subsequently duplexed in a primer extension reaction to minimize any effects of DNA secondary structure in selections. Libraries prepared using DNA ligation also yield dsDNA encoding sequences.

Figure 17:
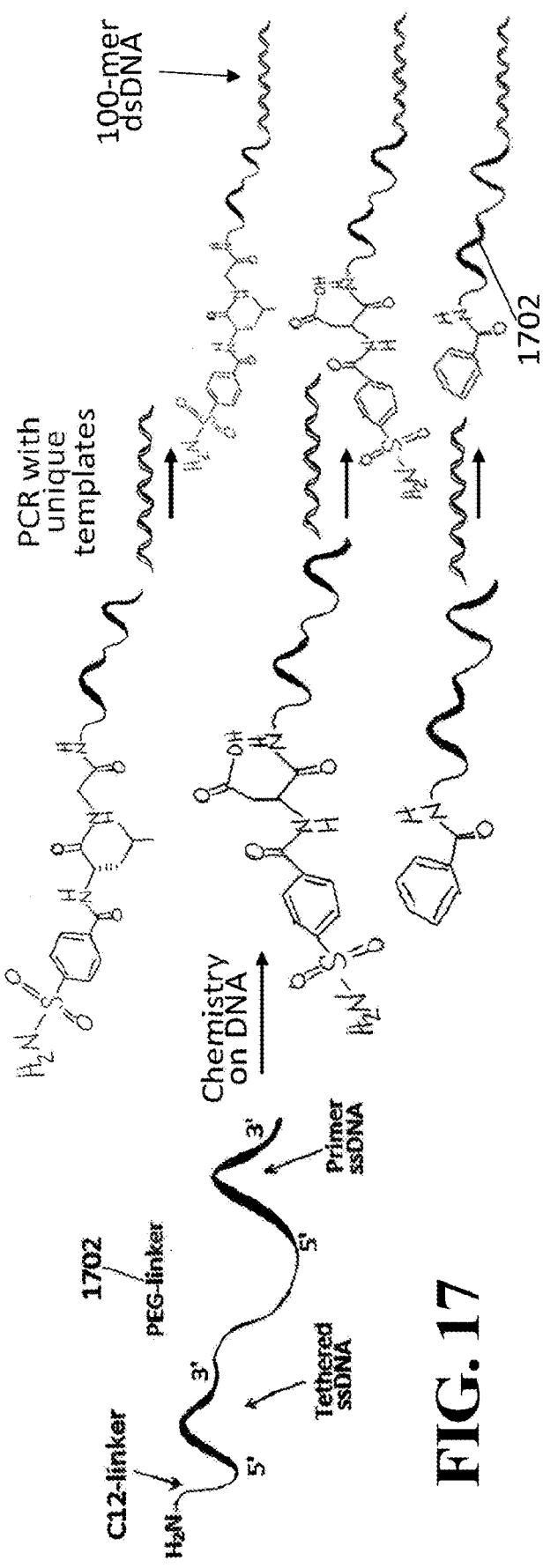
FIG. 17 shows a schematic representation of at exemplary embodiment of a method of the present disclosure for the preparation of ligands on DNA for crosslinking selections, with ligands synthesized separately on a linkered ssDNA 40-mer and used as primers in PCR to attach each ligand to a unique 100-mer DNA template.

To address this, in at least one embodiment of method 1300, a starting oligonucleotide is used that contains a polyethylene glycol (PEG) spacer between two oligo segments. Now referring to FIG. 17, a schematic is shown depicting an alternative method for the preparation of ligands 1302 on DNA 1304 for crosslinking selections. There, a PEG spacer 1702 results in a dsDNA encoding sequence tethered to a ssDNA sequence 1306 via the spacer 1702. This ssDNA contains the small molecule 1302 at its 5' end and is available for hybridization to a complementary, reactive group oligo 1314. The spacer prevents read-through of the appended ssDNA by DNA polymerase in a primer extension, and the 5' and 3'-end modifications of the tethered ssDNA 1306 prevents any interference in encoding by DNA ligation.

To prepare constructs for test selections, two CAII ligands and a non-ligand control (FIG. 17) were synthesized on a 5'-amine-modified, 40-mer oligonucleotide, which contained a PEG spacer between two 20-mer sequences as previously described. Using these oligos as primers in a PCR with unique 100-mer templates gave 100-mer dsDNA products tethered to the ligand-containing 20-mer ssDNA. DNA templates assigned to each ligand 1302 contained a unique, internal 20-mer sequence for use as a specific priming site to enable qPCR analysis of ligand enrichments. A mock library was then prepared by mixing ligand constructs GL-CBS and D-CBS at 0.1 nM each with an excess of control, non-ligand construct (Bz) (10 nM).

Using this mixture, test selections were conducted using the crosslinking approach with the sulfonyl fluoride oligo or using a traditional solid-phase selection with CAII immobilized on magnetic beads. For both selections, an approximate protein concentration of 1 μM was used to pose a challenge for the enrichment of the low affinity ligand, D-CBS ($K_d$=4.5 μM).

For the crosslinking selection, the DNA-conjugate mixture was equilibrated with a biotinylated CAII in solution. Then a 3'-modified ssDNA with sulfonyl fluoride (3) (reacting group 1314) complementary to the tethered ssDNA was added in slight excess of all DNA constructs (150 nM) for crosslinking to the target protein 1312. After overnight incubation, the proteins were denatured with SDS (while maintaining DNA hybridization) and the target protein 1312 was captured with streptavidin magnetic beads (purification step 1352). Taking advantage of the crosslinking, extensive and stringent washes of the beads was performed.

TABLE 1

Enrichment and recovery of small molecule-DNA conjugates from sulfonyl fluoride (3)-based crosslinking or solid-phase affinity selections for ligands binding to B. CAII. Enrichment is given as the fold change in concentration of each ligand-DNA construct relative to the non-ligand (Bz) DNA construct. Recovery is given as the amount of DNA recovered of the initial DNA mixture.

| | SDS + Stringent Washes | | Solid Phase Affinity Pull down | |
| --- | --- | --- | --- | --- |
| | X-linking with 3 1 μM CAII Enrichment (Recovery) | Without X-linking 1 μM CAII Enrichment (Recovery) | 1 μM CAII Enrichment (Recovery) | 17 μM CAII Enrichment (Recovery) |
| GL-CBS ($K_d$ 120 nM) | 17,000 (11%) | 22 (0.021%) | 720 (52%) | 610 (89%) |
| D-CBS ($K_d$ 4.5 μM) | 1,700 (1.1%) | 28 (0.026%) | 2.2 (0.16%) | 25 (3.6%) |
| Bz (non-ligand) | (0.00062%) | (0.00094%) | (0.073%) | (0.15%) |

Using qPCR to quantify the mixtures before and after selection, the crosslinking approach yielded 17,000-fold enrichment of the high affinity ligand, GL-CBS, and 1700-fold enrichment of the low affinity ligand, D-CBS, relative to the non-ligand, Bz, construct (step 1354) (see Table 1). The trend in enrichment was consistent with the differences in crosslinking yields observed at 1 μM CAII in FIG. 14C. The enrichment of both ligands was dependent on the crosslinking. A replica experiment lacking the reactive group (3'-OH ssDNA) failed to produce significant enrichments or ligand-DNA recovery (Table 1).

In comparison, the traditional solid-phase affinity selection enriched the high affinity ligand 720-fold, but did not enrich the low affinity ligand significantly. Failure to enrich the D-CBS ligand was anticipated in this selection given the dissociation constant is about 5-fold above the protein concentration used. With this selection containing an initial binding step and five bead washes (6 total partitioning cycles), the best case recovery of this ligand could be estimated at 0.002% ($0.17^6$), which is well below the observed background recovery of non-ligands. In contrast, the crosslinking selection involves just a single partitioning step, which is slightly less efficient due to crosslinking yields.

An additional solid-phase test selection was performed at much higher (estimated 17 μM) protein concentration (Table 1). In this case, enrichment of both ligands was detected, and the relative recovery of the GL-CBS and D-CBS ligands observed was consistent with their $K_d$'s, the number of partitioning cycles, and the estimated protein concentration. While the recovery of ligand-DNA was as good or greater than observed with crosslinking, the non-ligand recovery was also greater due to the less stringent washing conditions, which lessened the overall enrichment.

In the crosslinking-based test selection, a biotin affinity tag 1340 introduced by NHS-coupling on CAII was used to purify the DNAs crosslinked to the protein target 1312. The stability of the biotin-streptavidin interaction to relatively high levels of SDS makes this system particularly suitable for this application. While acylation of proteins with biotin is a commonly employed approach for immobilization of selection targets, it is not suitable for many proteins. A milder alternative would be the BirA tag, which allows for enzymatic biotinylation through a short peptide tag. Additionally, other affinity tags 1340 can be used under denaturing conditions, such as His6-Ni-NTA. Also, immunopurifications using various epitope tags 1340 can be performed on denatured proteins after appropriate dilution of denaturants.

Both the absolute recovery and relative enrichment of ligands are key considerations in the development of selection strategies. While the traditional, solid-phase selection (Table 1) did provide approximately 5-fold greater recovery of the high affinity GL-CBS ligand compared to the crosslinking selection, the overall enrichment was 20-fold lower. The lower recovery in the crosslinking case is likely a result of the crosslinking and protein capture efficiencies. The crosslinking approach clearly benefited from stringent washes, which reduced the background recovery of the non-ligand, Bz, construct 100-fold over the standard selection. Due to the typically high complexity of DNA-encoded libraries, selection methods must produce a high level of enrichment of ligands over non-ligands. The enrichment required is case dependent and is a function of the library complexity size and the number of DNA sequence reads obtainable. As each member in a DNA-encoded library may only be present at thousands of molecules each, high enrichment should not be achieved at the expense of ligand recovery. Large losses of DNA-linked ligands would lead to under sampling of the population. Since the concentration of each library member in a selection is insignificantly low, the free ligand to protein-bound ligand ratio is equal to the ratio of the $K_d$ to the protein concentration. As this ratio becomes much greater than 1, significant enrichment becomes difficult to achieve with solid-phase selections without incurring dramatic losses of ligands.

Since DNA-encoded libraries are an expensive resource, it is desirable to minimize the amount used. The model selection results demonstrate the potential for crosslinking to improve selections of DNA-encoded libraries, at least in part because ligands with binding affinity may be identified. This approach could be particularly useful in cases where the dissociation constants ($K_d$'s) of ligands are significantly greater than the target protein concentration. This may arise because of difficulties in obtaining a concentrated target protein. Many proteins are prone to aggregation at high concentration. Targeting of unpurified, dilute proteins directly in cell lysates, where the context may be critical for protein function, may be desirable. Additionally, crosslinking may allow discovery of very low affinity ($K_d$>10 μM) fragment ligands from DNA-encoded libraries.

The novel approach to crosslinking of method 1300 could also show utility in various DNA-based assay platforms for detecting and characterizing binding to proteins. Validation, qualitative, or quantitative ranking of protein binding for ligands on DNA could be conducted by simple gel-based assays (analogous to gel-shift assays with DNA-binding proteins), which require only pmol or less quantities for detection. Indeed, the crosslinking method 1300 could be applied in recently developed methods for highly multiplexed protein interaction detection by parallel DNA sequencing, such as single-molecular-interaction sequencing (SMI-seq) or parallel analysis of translated ORFs (PLATO).

In summary, the method 1300 applies crosslinking to the selection of ligands from DNA-encoded libraries, as well as detecting ligand binding affinity. Employing a tethered ssDNA construct 1306 allows for a reactive group 1314 to be synthesized separately and appended to DNA-encoded ligands 1310 after equilibration with protein targets 1312. The sufficient crosslinking yields and the ability to perform stringent washes after protein denaturation results in improved enrichments of DNA-linked ligands 1310 in a model selection. The technique is amenable to DNA-encoded libraries produced from a number of platforms and shows promise for enrichment of low affinity ligands and protein targets obtainable only at low concentrations.

Experimental Notes for Crosslinking Embodiments.

DNA conjugates were purified on a Varian Pro Star HPLC system and analytical analysis on an Agilent 1100 series HPLC system, both using Agilent Microsorb-MV 300-5 C18 250×4.6 mm reverse phase columns. Analytical separations were performed using 100 mM triethylammonium acetate (TEAA), pH 5.5 in water (A) or 100 mM triethylammonium acetate in 90% MeCN (B) with a linear gradient from 5-60% B over 22 minutes. Purifications were performed using the previous or 0.75% (v/v) 1,1,1,3,3,3-hexafluoropropan-2-ol, and 10 μM EDTA to pH 7.0 with triethylamine in water (A) or 90% MeOH (B) with a linear gradient from 5-50% B over 22 minutes. ESI-MS analysis was completed using an ABSciex 4500 QTrap from fractions collected from HFIP-based HPLC purifications. MALDI analysis was completed on an Applied Biosystems Voyager DE PRO instrument operated by the Purdue University Campus-Wide Mass Spectrometry Center after TEAA-based purification, ethanol precipitation, and ZipTip cleanup. On-DNA ligand dissociation constants were determined using a ForteBio Octet Red384. NMR analysis were completed on a Bruker ARX300 instrument as part of the Purdue Interdepartmental NMR Facility. All gel images were recorded by a GE Healthcare Typhoon Trio+ with gel band quantifications determined using ImageJ software.

General Procedure for Acylation of Amine-Modified ssDNA.

Acylation of amine-modified ssDNA was completed using a general procedure, modified from Halpin et al. A solution of 1 nmol of amine-modified ssDNA in 1 mL of DEAE bind buffer (10 mM HOAc, 0.005% Triton X-100) was immobilized onto 200 μL of 50% DEAE Sepharose slurry, pre-washed with DEAE Bind Buffer on a DNA solid-phase cartridge using a vacuum manifold. The immobilized DNA-containing cartridge was washed with 3 mL MeOH on the vacuum manifold and then the cartridge was placed between two 1 mL syringes. The carboxylic acid coupling reaction mixture of 40% DMF in MeOH with 50 mM carboxylic acid, 50 mM EDC-HCl, and 5 mM HOAt was pulled up by one syringe and passed back and forth through the column several times and then incubated for 30 minutes at RT, after which the reaction mixture was eluted on the vacuum manifold. A fresh reaction mixture was prepared and added to the cartridge and incubated for 30 minutes at RT. After elution of the second reaction mixture, the cartridge was washed with 3 mL DMF, 3 mL MeOH, and 1 mL DEAE bind buffer. The modified oligo was then eluted with 1 mL DEAE elution buffer (1.5 M NaCl, 100 mM TEAA, pH 5.5, 0.005% Triton X-100) and purified by HPLC.

General Procedure for Alkynyl Reactive Group Coupling to ssDNA'-3'-$N_3$.

Performed using a modified procedure known in the art (see e.g., Hong et al., Angew. Chemi—Int. Ed., 2009, 48: 9879-9883) under general conditions are as follows: 1.0 μM ssDNA'-3'-$N_3$ was added to 50 mM sodium phosphate, pH 7.4, 150 mM NaCl, 5 mM aminoguanidinium hydrochloride, 5% (v/v) 5:1 50 mM THPHA:50 mM $CuSO_4$ (premixed), 1 mM alkyne, and 5 mM sodium ascorbate with a final concentration of 5% (v/v) DMSO. The mixture was incubated for 20 minutes at RT and then concentrated and excess organics removed through 1-butanol extractions. The resulting aqueous mixture was used directly for crosslinking experiments.

General Procedure for Electrophilic Crosslinking.

The target protein (1.0 μM) and BSA (1.0 μM) in 0.1 M sodium phosphate, pH 8, 0.25 M NaCl, 0.02% (v/v) Tween-20, was combined with the ligand-ssDNA conjugate (1.0 μM) and incubates for 30 minutes prior to the addition of the reactive group-ssDNA (0.75 μM). Electrophilic crosslinking was allowed to proceed 16 h at RT, quenched by the addition of 6×SDS-loading buffer, and directly analyzed by SDS-PAGE. Gels were imaged immediately for FAM fluorescence and then Coomassie stained.

General Procedure for Photocrosslinking.

Photocrosslinking was performed as described above, except the system was allowed to incubate with both the ligand-ssDNA and reactive group-ssDNA' for 30 minutes at RT. Irradiation was completed by exposure to a 4W 356 nm UV light source at 4° C. for 1 hour, quenched by the addition 6×SDS-loading buffer, and directly analyzed by SDS-PAGE. Gels were imaged immediately for FAM fluorescence and then Coomassie stained.

General Procedure for Enrichment of Ligands Via Crosslinking (SDS+Stringent Washes).

A premix of ligand-dsDNA and non-ligand-dsDNA (0.11 nM and 10 nM, respectively) was added to 1.0 μM biotinylated B. CAII and 10 μM BSA in 0.1 M sodium phosphate, pH 8.0, 0.25 M NaCl, 0.02% (v/v) Tween-20, 1.0 mg/mL tRNA and incubated at RT for 30 min. Meanwhile, the reactive group ssDNA was prepared as described above (General procedure for alkynyl reactive group coupling to ssDNA'-3'-$N_3$). The ssDNA'-3'-reactive group was added in 15× excess of ligand and non-ligand DNA to the protein/DNA mixture and incubated 16 h at RT. SDS was added to a final concentration of 5.0% (w/v) and the mixture was incubated for 30 min at RT, diluted with the above buffer to a final SDS concentration of 1.0% (w/v) and incubated with pre-washed Nanolink Streptavidin Magnetic Beads (1.5× based on capacity) for 2 h. The magnetic beads were then separated and supernatant removed. The magnetic beads were then washed with the above buffer+0.1% (w/v) SDS five times. Following the final wash, the magnetic beads were eluted by suspending in 10 μL water and heated at 95° C. for 5 minutes. qPCR analysis of the premix and magnetic bead elution was completed by comparison of CT standard curves of identical dsDNA constructs.

General Procedure for Enrichment of Ligands Via Solid-Phase Affinity Pulldowns.

Biotinylated B. CAII (1.2× based on magnetic bead capacity) was immobilized onto pre-washed Nanolink Streptavidin Magnetic Beads by incubating in 0.1 M sodium phosphate, pH 8.0, 0.25 M NaCl, 0.02% (v/v) Tween-20, 1.0 mg/mL tRNA, 10 μM BSA for 2 h at RT. The magnetic beads were then separated and supernatant removed. The CAII-bound magnetic beads were then washed with the above buffer three times and a premix of ligand-dsDNA and non-ligand-dsDNA (0.1 nM and 10 nM, respectively) in the above buffer (in the appropriate volume to give the desired effective protein concentration) was added and incubated at RT for 1.5 h. The magnetic beads were then separated and DNA supernatant removed. The CAII-bound magnetic beads were then washed with the above buffer five times, maintaining the same effective protein concentration in each wash. After the final wash, the magnetic beads were suspended in 10 water and heated at 95° C. for 5 min. qPCR analysis of the premix and magnetic bead elution was completed by comparison of CT standard curves of identical dsDNA constructs.

While embodiments of the kits, systems and methods herein have been described in considerable detail, such embodiments are merely offered by way of non-limiting examples. It will be understood that various changes and modifications may be made, and equivalents substituted for elements thereof, without departing from the scope of the disclosure. This disclosure is not intended to be exhaustive or to limit its scope. Further, in describing representative embodiments, the disclosure may have presented a method and/or process as a particular sequence of steps; however, to the extent that the method/process does not rely on the particular order of steps set forth herein, it should not be limited to the particular sequence of steps described as other sequences may be possible. Therefore, the particular order of the steps disclosed herein should not be construed as limiting. In addition, disclosure directed to a method and/or process should not be limited to the performance of their steps in the order written. Such sequences may be varied and still remain within the scope of the present disclosure.

The invention claimed is:

1. A method for detecting proteomic activity in a sample comprising active proteins, the method comprising the steps of:

providing a population of probes, each of the probes comprising a substrate linked to a DNA construct, the DNA construct comprising one or more amplifiable identification barcode regions, wherein at least one of the barcode regions of the double-stranded DNA is unique;

contacting the population of probes with the sample comprising active proteins in an initial pool and under conditions and for a sufficient time to allow said protein to turnover via chemical transformation of the substrate of a probe into a product wherein the protein comprises a farnesyltransferase, a protein kinase, or a protease;

quenching protein activity within the initial pool;

combining the probes from multiple samples into an initial pool;

separating the DNA probe constructs of the initial pool that are linked to the product or that are linked to the protein to form a purified pool, wherein the separating is performed by selectively linking a tag to said probes, wherein the tag is appended utilizing chemical or biochemical steps that selectively modify product molecules, but not substrate molecules, or wherein the tag is appended using chemical or biochemical steps that selectively modify substrate molecules, but not product molecules, and wherein the tag comprises a moiety for selective affinity purification;

quantifying the DNA constructs of the initial pool and the DNA constructs of the purified pool by quantitative PCR, parallel DNA sequencing or high-throughput DNA sequencing; and detecting the presence or absence of a detectable signal in the quantified DNA constructs, the detectable signal comprising identifying a change in probe frequency between the initial pool and the purified pool.

2. The method of claim 1, wherein the step of quantifying the DNA constructs of the initial pool further comprises determining a probe abundance measurement for the initial pool and a probe abundance measurement for the purified pool, and wherein the detectable signal comprises a change in the probe abundance measurements between the initial pool and the purified pool.

3. The method of claim 1, wherein the step of separating the DNA probe constructs of the initial pool that are linked product to form a purified pool further comprises the steps of:

reserving a sample of the initial pool, wherein the initial pool further comprises a population of control probes, each of the control probes comprising either a control product or control unreacted substrate linked to a DNA construct comprising one or more amplifiable identification barcode;

determining the relative abundance of DNA constructs of the initial pool and the purified pool by quantitative PCR, parallel DNA sequencing or high-throughput DNA sequencing.

4. The method of claim 1, wherein an amplifiable identification barcode region of each DNA construct identifies a source of the sample comprising the protein.

5. The method of claim 2, wherein the initial pool further comprises a population of control probes, each of the control probes comprising either a control product or substrate linked to a DNA construct comprising one or more amplifiable identification barcode regions, and further comprising the steps of separating the DNA constructs of the initial pool that are linked to the control product or control substrate.

6. The method of claim 5, wherein:

the step of separating the DNA constructs of the initial pool that are linked to the control product or control substrate to form a purified pool further comprises quantifying the DNA constructs within the purified pool; and the step of detecting the presence or absence of a detectable signal further comprises comparing the probe abundance measurement for the purified pool with a probe abundance measurement within the initial pool and comparing to the abundance changes of the control probes between the purified and initial pools.

7. The method of claim 1, further comprising the steps of isolating the DNA constructs of the probes of a sample of the initial pool and isolating the DNA constructs of the probes within the purified pool; and wherein the step of quantifying the DNA constructs of the initial pool and the DNA constructs of the purified pool further comprises performing a quantitative polymerase chain reaction assay on the DNA constructs of the sample of the initial pool and the DNA constructs of the purified pool.

8. The method of claim 7, wherein the step of detecting the presence or absence of a detectable signal comprises comparing the quantitative polymerase chain reaction results of the sample of the initial pool and the purified pool.

9. The method of claim 1, wherein a correlation exists between probe abundance change and the functional activity of the protein of a sample, where the probe abundance change is determined as a ratio between a first probe abundance measurement of the probe in the purified pool as compared to a second probe abundance measurement of the probe in the initial pool, wherein as the ratio approaching 1 is indicative of functional activity of the protein of said sample.

10. The method of claim 1, wherein where the protein of a sample comprises an enzyme, a low correlation between the probe abundance measurement of the initial pool and the probe abundance measurement of the purified pool is indicative of enzyme inhibition of the protein of said sample.

11. The method of claim 1, wherein the proteomic function comprises enzymatic activity of the protein of said sample.

12. The method of claim 1, wherein:

the population of probes comprises a first subset of probes comprising a first substrate specific to a first target protein and a second subset of probes comprising a second substrate specific to a second target protein; and the step of contacting the population of probes with a sample further comprises contacting the first subset of probes with a first sample comprising the first target protein and the second subset of probes with a second sample comprising the second target protein under conditions and for sufficient time to allow the target protein to react with the respective substrate.

13. The method of claim 12, further comprising the step of pooling the first subset of probes and the first sample with the second subset of probes and the second sample to form the initial pool and wherein each probe of the first subset has information associated with at least one amplifiable identification barcode region thereof identifying of the first subset and each probe of the second subset has information associated with at least one amplifiable identification barcode region thereof identifying of the second subset.

14. The method of claim 1, further comprising the step of selectively labeling the product of each probe.

15. The method of claim 14, wherein the step of selectively labeling the product of each probe is performed via chemical biotinylation.

16. The method of claim 1, wherein the proteomic function to be detected comprises enzyme activity and the substrate comprises an enzyme substrate.

17. The method of claim 1, wherein the linker of the DNA-encoded probe is selected from a group consisting of an oligonucleotide, a modified oligonucleotide, and a primer.

18. The method of claim 16, further comprising the step of synthesizing the probes by:
   attaching a substrate to a linker to form an oligonucleotide-substrate conjugate; and
   appending the substrate of the oligonucleotide-substrate conjugate to a double-stranded DNA having one or more unique amplifiable identification barcode regions for associating with the substrate.

19. The method of claim 1, wherein the step of separating the probes that comprise product-DNA conjugates from the initial population comprises the use of streptavidin magnetic beads.

20. The method of claim 16, wherein the step of providing a population of probes further comprises the steps of:
   chemically synthesizing an oligonucleotide-substrate conjugate; and
   hybridizing the oligonucleotide-substrate conjugate to a DNA construct.

21. The method of claim 1, wherein the step of chemically synthesizing an oligonucleotide-substrate conjugate comprises direct peptide synthesis on amine-modified oligonucleotides or post synthetic conjugation using copper-catalyzed azide-alkyne cycloaddition.

22. The method of claim 1, wherein the step of providing a population of probes further comprises the step of hybridizing an activity-based protein profiling probe to a double-stranded DNA construct comprising an accepting single-stranded DNA strand.

23. The method of claim 22, wherein the activity-based protein profiling probe comprises a warhead, a specificity element, and an affinity label.

* * * * *